US010527620B2

(12) United States Patent
Broide et al.

(10) Patent No.: US 10,527,620 B2
(45) Date of Patent: *Jan. 7, 2020

(54) METHOD OF DETECTING CLEAVED SNAP25 IN TISSUE SAMPLES

(71) Applicant: Allergan, Inc., Irvine, CA (US)

(72) Inventors: Ron S. Broide, San Marcos, CA (US); Brian Cai, Irvine, CA (US); Ester Fernandez-Salas, Ann Arbor, MI (US); Joseph Francis, Laguna Niguel, CA (US); Catherine Rheaume, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 583 days.

This patent is subject to a terminal disclaimer.

(21) Appl. No.: 14/792,795

(22) Filed: Jul. 7, 2015

(65) Prior Publication Data

US 2016/0003824 A1 Jan. 7, 2016

Related U.S. Application Data

(60) Provisional application No. 62/021,379, filed on Jul. 7, 2014, provisional application No. 62/158,900, filed on May 8, 2015, provisional application No. 62/163,829, filed on May 19, 2015.

(51) Int. Cl.
*G01N 33/573* (2006.01)
*C07K 16/18* (2006.01)

(52) U.S. Cl.
CPC ........... *G01N 33/573* (2013.01); *C07K 16/18* (2013.01); *C07K 2317/24* (2013.01); *C07K 2317/34* (2013.01); *C07K 2317/567* (2013.01); *C07K 2317/72* (2013.01); *G01N 2333/952* (2013.01)

(58) Field of Classification Search
None
See application file for complete search history.

(56) References Cited

U.S. PATENT DOCUMENTS 4,816,567 A * 3/1989 Cabilly .............. C07K 16/3007 435/252.3
5,962,637 A 10/1999 Shone et al.
6,337,386 B1 1/2002 Shone et al.
7,183,066 B2 2/2007 Femandez-Salas
7,208,285 B2 4/2007 Steward
7,332,567 B2 2/2008 Steward
7,399,607 B2 7/2008 Williams
7,598,027 B2 10/2009 Femandez-Salas
7,632,655 B2 12/2009 Williams
7,635,574 B2 12/2009 Williams
7,638,294 B2 12/2009 Williams
7,645,570 B2 1/2010 Femandez-Salas
7,674,601 B2 3/2010 Williams
7,678,550 B1 3/2010 Steward
7,709,608 B2 5/2010 Steward et al.
7,718,766 B2 5/2010 Steward
7,749,759 B2 7/2010 Femandez-Salas
8,198,034 B2 6/2012 Fernandez-Salas et al.
8,361,789 B2 1/2013 Zhu et al.
8,618,261 B2 * 12/2013 Ester ........................ C12Q 1/37 530/387.1
2004/0219619 A1 11/2004 Femandez-Sala
2005/0069556 A1 * 3/2005 Felici ...................... C40B 40/02 424/185.1
2008/0160561 A1 7/2008 Fernandez-Salas et al.
2010/0203559 A1 * 8/2010 Ester .................. C07K 16/1282 435/7.92
2010/0233741 A1 * 9/2010 Wang ....................... C12Q 1/37 435/7.94
2012/0225436 A1 9/2012 Femandez-Salas

FOREIGN PATENT DOCUMENTS

WO WO1995-33850 A1 12/1995
WO WO1996033273 A1 10/1996
WO WO2006042149 4/2006
WO WO2009039356 3/2009
WO WO2009-114748 9/2009
WO WO2010105236 9/2010

OTHER PUBLICATIONS

Rudikoff et al., Single amino acid substitution altering antigen-binding specificity, Proc Natl Acad Sci USA 1982 vol. 79 p. 1979-1983 (Year: 1982).*
Pascalis et al., Grafting of "abbreviated" complementarity-determining regions containing specificity-determining residues essential for ligand contact to engineer a less immunogenic humanized monoclonal antibody, The Journal of Immunology (2002) 169, 3076-3084 (Year: 2002).*
Casset et al., A peptide mimetic of an anti-CD4 monoclonal antibody by rational design, (2003) BBRC 307, 198-205 (Year: 2003).*
Van Regenmortel, Molecular dissection of protein antigens and the prediction of epitopes, Chapter 1 in: Laboratory Techniques in Biochemistry and Molecular Biology vol. 19, 1988, pp. 1-39 (Year: 1988).*
Adler, Sarah et al, The Current Scientific and Legal Status of Alternative Methods to the LD50 Test for Botulinum Neurotoxin Potency Testing, ATLA, 2010, 315-330, 38.

(Continued)

*Primary Examiner* — Christine Foster
*Assistant Examiner* — Ellen J Marcsisin
(74) *Attorney, Agent, or Firm* — Brigitte C. Phan

(57) ABSTRACT

Methods and compositions for detecting BoNT/A enzymatic activity in tissues or a tissue sample are described herein. The invention encompasses antibodies that bind preferentially to BoNT/A cleaved SNAP25 and is able to preferentially detect BoNT/A cleaved SNAP25, as compared to intact (non-cleaved) SNAP25, in a tissue sample.

11 Claims, 10 Drawing Sheets
(7 of 10 Drawing Sheet(s) Filed in Color)
Specification includes a Sequence Listing.

(56) References Cited

OTHER PUBLICATIONS

Amersdorfer, Peter et al, Molecular Characterization of Murine Humoral Immune Response to Botulinum Neurotoxin Type A Binding Domain as Assessed by Using Phage Antibody Libraries, Infect Immun, Sep. 1997, 3743-3752, 65(9).
Aoki, K.R. and Francis, J., (2011). "Updates on the antinociceptive mechanism hypothesis of botulinum toxin A." Parkinsonism.Relat Disord. 17 Suppl 1, S28-S33.
Boyd, Robert et al, The Effects of Botulinum Neurotoxins on the Release of Insulin From the Insulinoma Cell Lines HIT-15 and RINm5F, The Journal of Biological Chemistry, 1995, 18216-18218, 270 (31).
Capek, et al., Sensing the Deadliest Toxin: Technologies for Botulinum Neurotoxin Detection, Toxins 2010, 2, 24-53.
Fernandez-Salas, Ester et al, Botulinum Neurotoxin Serotype a Specific Cell-Based Potency Assay to Replace the Mouse Bioassay, PLOS ONE, Nov. 2012, 1-13, 7 (11).
Foran, Patrick et al, Botulinum Neurotoxin C1 Cleaves Both Syntaxin and SNAP-25 in Intact and Permeabilized Chromaffin Cells: Correlation With Its Blockade of Catecholamine Release, Biochemistry, 1996, 2630-2636, 35.
Grate, et al., Advances in assays and analytical, Trends in Analytical Chemistry, 2010, 1137-1156, 29(10).
Grunfeld, A, Murray, C.A., and Solish, N., (2009). "Botulinum toxin for hyperhidrosis: a review." Am.J.Clin.Dermatol. 10, 87-102, Abstract Only (1 page).
Jacky, Birgitte et al, Identification of Bibroblast Growth Factor Receptor 3 (FGFR3) as a Protein Receptor for Botulinum Neurotoxin Serotype A (BoNT/A), PLOS Pathogens, May 2013, 1-17, 9(5).
Marconi, et al., A Protein Chip Membrane-Capture Assay for Botulinum Neurotoxin Activity, Toxicology and Applied Pharmacology, 2008, 439-446.
Marini, et al., SiMa, a New Neuroblastoma Cell Line Combining Poor Prognostic Cytogenetic Markers with High Adrenergic Differentiation, Cancer Genet Cytogenet, 1999, 161-164, 112, Elsevier Science Inc., NY.
Montal, Botulinum neurotoxin: a marvel of protein design, Parkinsonism Relat Disord, 2010, S28-S33, pp. 591-617.
Mort, J.S. and Buttle, D.J., (1999). "The use of cleavage site specific antibodies to delineate protein processing and breakdown pathways." Mol.Pathol. 52, 11-18.
Mort, J.S., Flannery, C.R., Makkerh, J., Krupa, J.C., and Lee, E.R, 2003. Use of anti-neoepitope antibodies for the analysis of degradative events in cartilage and the molecular basis for neoepitope specificity. Biochem.Soc.Symp. 107-11, pp. 107-114.
Nagata, K., Izawa, I., and Inagaki, M., 2001. A decade of site- and phosphorylation state-specific antibodies: recent advances in studies of spatiotemporal protein phosphorylation. Genes Cells 6, 653-664.
Ornberg, et al., Western Blot Analysis with Quantum Dot Fluorescence Technology: A Sensitive and Quantitative Method for Multiplexed Proteomics, Nature Methods, Jan. 2005, 79-81, 2(1), Natures Publishing Group.
R.G.A. Jones, et al., Development of Improved SNAP25 Endopeptidase Immuno-Assays for Botulinum Type A and E Toxins, Journal of Immunological Methods, 2008, 92-101, 329, Elsevier, US.
Ramirez-Castaneda, J. and Jankovic, J., (2014). "Long-term efficacy, safety, and side effect profile of botulinum toxin in dystonia: a 20-year follow-up." Toxicon 90, 344-348.
Rheaume, Catherine et al, A Highly Specific Monoclonal Antibody for Botulinum Neurotoxin Type A-Cleaved SNAP25, Toxins, 2015, 2354-2370, 7.
Using fluorescent sensors to detect botulinum neurotoxin activity in vitro and in living cells, PNAS, Oct. 2004, pp. 14701-14706, vol. 101, No. 41, The National Academy of Sciences.
Williamson et al, Clostridial Neurotoxins and Substrate Proteolysis in Intact Neurons, The Journal of Biological Chemistry, 1996, 7694-7699, vol. 271, No. 13.
Yablon, S.A., Brin, M.E, VanDenburgh, A.M., Zhou, J., Garabedian-Ruffalo, S.M., Abu-Shakra, S., and Beddingfield, F.C., III (2011). "Dose response with onabotulinumtoxinA for post-stroke spasticity: a pooled data analysis." Mov Disord. 26, 209-215.
Fernandez-Salas, Ester, et al., Is the Light Chain Subcellular Localization an Important Factor in Botulinum Toxin Duration of Action?, Movement Disorders, 2004, S23-S34, vol. 19, Suppl. 8.
Garcia-Rodriguez, Consuelo, et al., Molecular Evolution of Antibody Cross-Reactivity for Two Subtypes of Type A Botulinum Neurotoxin, Nature Biotechnology, 2007, 107-116, 25(1), Nature Publishing Group, US.
Gaynor, Bruce, et al., Presumed Activation of Herpectic Keratouveitis After Argon Laser Peripheral Iridotomy, AmerJoum, 2000, 665-667, 130(5).
Hakami, Ramin et al., Gaining Ground: Assays for Therapeutics against botulinum neurotoxin, Cel Press, 2010, 164-172, vol. 18, No. 4.
Nabokina, Svetlana, et al., Intracellular Location of SNAP-25 in Human Neutrophils, Biochem, 1997, 592-597, 239.
Rasooly, Reuven et al., Development of an In Vitro Activity Assay as an Alternative to the Mouse Bioassay for Clostridium Botulinum Neurotoxin Type A, Applied and Environmental MicroBiology, 2008, 4309-4313, 74(14).
Schulte-Baukloh, Heinrich et al., Persistence of the Synaptosomal-Associated Protein-25 Cleavage Product After Intradetrusor Botulinum Toxin A Injections in Patients with Myelomeningocele Showing an Inadequate Response to Treatment, BJU International, 2007, 1075-1080, 100 (5).
Shimazaki, Youji et al., Phosphorylation of 25-kDa Synaptosome-Associated Protein, The Journal of Biological Chemistry, 1996, 14548-14553, vol. 271, No. 24.
Burstein, Rami, et al., Selective Inhibition of meningeal Nociceptors by Botulinum Neurotoxin Type A: Therapeutic Implications for Migraine and Other Pains, Cephalalgia, 2014, vol. 34(11), 853-869.
Hallis, Bassam, et al., Development of Novel Assays for Botulinum Type A and B Neurotoxins Based on Their Endopeptidase Activities, Journal of Clinical Microbiology, 1996, vol. 34 (8), 1934-1938.
Ekong, Theresa A. N., Recombinant SNAP-25 is an effective substrate for Clostridium botulinum type A toxin endopeptidase activity in vitro, 1997.
Fernandez-Salas, E., et al, Plasma membrane localization signals in the light chain of botulinum neurotoxin, PNAS, 2004, 3208-3213, 101 (9).

* cited by examiner

```
                        SEQUENCE LISTING


<160> NUMBER OF SEQ ID NOS: 9

<210> SEQ ID NO 1
<211> LENGTH: 219
<212> TYPE: PRT
<213> ORGANISM: Mus sp.

<400> SEQUENCE: 1

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asn Thr
            20                  25                  30

Asn Gly Lys Thr Tyr Leu Thr Trp Leu Ile Gln Arg Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Ser His Phe Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 2
<211> LENGTH: 112
<212> TYPE: PRT
<213> ORGANISM: Mus sp.

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asn Thr
            20                  25                  30

Asn Gly Lys Thr Tyr Leu Thr Trp Leu Ile Gln Arg Pro Gly Gln Ser
        35                  40                  45

Pro Gln Arg Leu Ile Tyr Leu Val Ser Lys Leu Asp Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Ser His Phe Pro Phe Thr Phe Gly Ser Gly Thr Lys Leu Glu Ile Lys
            100                 105                 110


<210> SEQ ID NO 3
<211> LENGTH: 436
<212> TYPE: PRT
<213> ORGANISM: Mus sp.

<400> SEQUENCE: 3

Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Val Tyr
65                  70                  75                  80

Met Tyr Leu Asn Ser Leu Thr Ser Glu Asp Ser Ala Val Tyr Phe Cys
                85                  90                  95

Lys Arg Met Gly Tyr Trp Gly Gln Gly Thr Thr Val Thr Val Ser Ser
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Glu Ser Asp Leu Tyr Thr Leu
                165                 170                 175

Ser Ser Ser Val Thr Val Pro Ser Ser Pro Arg Pro Ser Glu Thr Val
            180                 185                 190

Thr Cys Asn Val Ala His Pro Ala Ser Ser Thr Lys Val Asp Lys Lys
        195                 200                 205

Ile Val Pro Arg Asp Cys Gly Cys Lys Pro Cys Ile Cys Thr Val Pro
    210                 215                 220

Glu Val Ser Ser Val Phe Ile Phe Pro Pro Lys Pro Lys Asp Val Leu
225                 230                 235                 240

Thr Ile Thr Leu Thr Pro Lys Val Thr Cys Val Val Val Asp Ile Ser
                245                 250                 255

Lys Asp Asp Pro Glu Val Gln Phe Ser Trp Phe Val Asp Asp Val Glu
            260                 265                 270

Val His Thr Ala Gln Thr Gln Pro Arg Glu Glu Gln Phe Asn Ser Thr
        275                 280                 285

Phe Arg Ser Val Ser Glu Leu Pro Ile Met His Gln Asp Trp Leu Asn
    290                 295                 300

Gly Lys Glu Phe Lys Cys Arg Val Asn Ser Ala Ala Phe Pro Ala Pro
305                 310                 315                 320

Ile Glu Lys Thr Ile Ser Lys Thr Lys Gly Arg Pro Lys Ala Pro Gln
                325                 330                 335
```

-continued

Val Tyr Thr Ile Pro Pro Pro Lys Glu Gln Met Ala Lys Asp Lys Val
340 345 350

Ser Leu Thr Cys Met Ile Thr Asp Phe Phe Pro Glu Asp Ile Thr Val
355 360 365

Glu Trp Gln Trp Asn Gly Gln Pro Ala Glu Asn Tyr Lys Asn Thr Gln
370 375 380

Pro Ile Met Asn Thr Asn Gly Ser Tyr Phe Val Tyr Ser Lys Leu Asn
385 390 395 400

Val Gln Lys Ser Asn Trp Glu Ala Gly Asn Thr Phe Thr Cys Ser Val
405 410 415

Leu His Glu Gly Leu His Asn His His Thr Glu Lys Ser Leu Ser His
420 425 430

Ser Pro Gly Lys
435

<210> SEQ ID NO 4
<211> LENGTH: 112
<212> TYPE: PRT
<213> ORGANISM: Mus sp.

<400> SEQUENCE: 4

Gln Val Lys Leu Gln Glu Ser Gly Ala Glu Leu Val Lys Pro Gly Ala
1 5 10 15

Ser Val Lys Ile Ser Cys Lys Ala Ser Gly Tyr Thr Phe Thr Asp His
20 25 30

Ser Ile His Trp Val Lys Gln Lys Pro Gly Gln Gly Leu Glu Trp Ile
35 40 45

Gly Tyr Leu Phe Pro Gly Asn Gly Asn Phe Glu Tyr Asn Glu Lys Phe
50 55 60

Lys Gly Lys Ala Thr Leu Thr Ala Asp Lys Ser Ser Ser Thr Val Tyr
65 70 75 80

Met Tyr Leu Asn Ser Leu Thr Ser Glu Asp Ser Ala Val Tyr Phe Cys
85 90 95

Lys Arg Met Gly Tyr Trp Gly Gln Gly Thr Thr Val Thr Val Ser Ser
100 105 110

<210> SEQ ID NO 5
<211> LENGTH: 219
<212> TYPE: PRT
<213> ORGANISM: Homo sapiens

<400> SEQUENCE: 5

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asn Thr
20 25 30

Asn Gly Lys Thr Tyr Leu Thr Trp Leu Ile Gln Arg Pro Gly Gln Ser
35 40 45

Pro Gln Arg Leu Ile Tyr Leu Val Ser Lys Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Leu Gln Ser
85 90 95

Ser His Phe Pro Phe Thr Phe Gly Ser Gly Thr Lys Leu Glu Ile Lys
100 105 110

-continued

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 6
<211> LENGTH: 112
<212> TYPE: PRT
<213> ORGANISM: Homo sapiens

<400> SEQUENCE: 6

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asn Thr
            20                  25                  30

Asn Gly Lys Thr Tyr Leu Thr Trp Leu Ile Gln Arg Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Ser His Phe Pro Phe Thr Phe Gly Ser Gly Thr Lys Leu Glu Ile Lys
            100                 105                 110


<210> SEQ ID NO 7
<211> LENGTH: 442
<212> TYPE: PRT
<213> ORGANISM: Homo sapiens

<400> SEQUENCE: 7

Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Val Tyr
65                  70                  75                  80

Met Tyr Leu Asn Ser Leu Thr Ser Glu Asp Ser Ala Val Tyr Phe Cys
                85                  90                  95

Lys Arg Met Gly Tyr Trp Gly Gln Gly Thr Thr Val Thr Val Ser Ser
            100                 105                 110
```

-continued

```
Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 8
<211> LENGTH: 112
<212> TYPE: PRT
<213> ORGANISM: Homo sapiens

<400> SEQUENCE: 8

Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
```

-continued

```
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Val Tyr
65                  70                  75                  80

Met Tyr Leu Asn Ser Leu Thr Ser Glu Asp Ser Ala Val Tyr Phe Cys
                85                  90                  95

Lys Arg Met Gly Tyr Trp Gly Gln Gly Thr Thr Val Thr Val Ser Ser
            100                 105                 110


<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ser Asn Lys Thr Arg Ile Asp Glu Ala Asn Gln
1               5                   10
```

METHOD OF DETECTING CLEAVED SNAP25 IN TISSUE SAMPLES

CROSS REFERENCE TO RELATED APPLICATIONS

This application claims the benefit of U.S. Provisional Application Ser. Nos. 62/021,379 filed Jul. 7, 2014; 62/158,900 filed May 8, 2015; and 62/163,829 filed May 19, 2015, all incorporated entirely by reference.

TECHNICAL FIELD OF THE INVENTION

The present disclosure relates to methods and compositions for detecting cleaved SNAP25 in tissue samples, such as botulinum neurotoxin cleavage of SNAP25. The invention further provides for antibodies that bind to cleaved SNAP25, including the SNAP25 cleavage product by botulinum neurotoxin serotype A.

BACKGROUND OF THE INVENTION

The therapeutic utility of botulinum neurotoxin type A (BoNT/A) has grown considerably over the past several decades and Allergan's product, onabotulinumtoxinA, is now approved globally for 11 major therapeutic and cosmetic indications, including treatment for various neuromuscular disorders (Ramirez-Castaneda, J. and Jankovic, J., (2014). "Long-term efficacy, safety, and side effect profile of botulinum toxin in dystonia: a 20-year follow-up." *Toxicon* 90, 344-348.; Yablon, S. A., Brin, M. F., VanDenburgh, A. M., Zhou, J., Garabedian-Ruffalo, S. M., Abu-Shakra, S., and Beddingfield, F. C., III (2011). "Dose response with onabotulinumtoxinA for post-stroke spasticity: a pooled data analysis."*Mov Disord.* 26, 209-215.), smooth muscle and autonomic dysfunctions (Ellsworth, P. and Travis, M., (2014). "Onabotulinum toxin A: a therapeutic option for refractory neurogenic detrusor overactivity and idiopathic overactive bladder." *Urol. Nurs.* 34, 165-171.; Grunfeld, A., Murray, C. A., and Solish, N., (2009). "Botulinum toxin for hyperhidrosis: a review." *Am. J. Clin. Dermatol.* 10, 87-102.) and for nociceptive pain syndromes (Aoki, K. R. and Francis, J., (2011). "Updates on the antinociceptive mechanism hypothesis of botulinum toxin A." *Parkinsonism. Relat Disord.* 17 Suppl 1, S28-S33.; Burstein, R., Zhang, X., Levy, D., Aoki, K. R., and Brin, M. F., (2014). "Selective inhibition of meningeal nociceptors by botulinum neurotoxin type A: therapeutic implications for migraine and other pains." *Cephalalgia* 34, 853-869.).

While the general mechanism of action (MoA) for BoNT/A at the presynaptic nerve terminal is well established (Montal, M., (2010). "Botulinum neurotoxin: a marvel of protein design." *Annu. Rev. Biochem.* 79, 591-617.), there are still many unanswered questions regarding the intracellular trafficking patterns and general 'life-cycle' of the toxin. Resolving these questions partly depends on the ability to precisely detect the toxin's location, distribution, and movement within a cell. Direct detection of BoNT/A using antibodies is difficult due to its high potency and therefore, extremely low concentration within neurons. An alternative approach for detecting the presence of BoNT/A has been to track its enzymatic activity via immuno-staining for the cleaved SNAP25 product ($SNAP25_{197}$). Both commercial and proprietary antibodies have been used to trace the expression of full-length SNAP25 ($SNAP25_{206}$) or BoNT/A-cleaved SNAP25 ($SNAP25_{197}$). However, the terminal epitope of $SNAP25_{197}$ that is generated following BoNT/A cleavage is difficult to specifically target with an antibody without also recognizing the intact SNAP25 protein (Mort, J. S. and Buttle, D. J., (1999). "The use of cleavage site specific antibodies to delineate protein processing and breakdown pathways."*Mol. Pathol.* 52, 11-18.). Consequently, immuno-staining results have been misleading, with some antibodies being assay-dependent while other antibodies are tissue-specific. There is therefore a need for a very selective antibody against BoNT/A-cleaved SNAP25 that can identify $SNAP25_{197}$ in any tissue-type and in multiple assays following exposure to BoNT/A.

The present disclosure addresses these issues by providing methods and compositions for detecting botulinum toxin cleaved SNAP25, including BoNT/A cleaved SNAP25 and any other BoNT/A-related compounds that cleave SNAP25 at position '197', in various different assays, such as but not limited to immunohistochemistry using highly specific recombinant monoclonal antibodies (rMAb) against $SNAP25_{197}$. These antibodies can be used to detect $SNAP25_{197}$ in a variety of tissues from different species, such as but not limited to human. These antibodies can also be used as tools to diagnose activity and efficacy in tissues from humans that have been treated with neurotoxin, such as but not limited to onabotulinumtoxinA.

SUMMARY OF THE INVENTION

The invention encompasses an anti-SNAP25 antibody wherein the antibody binds preferentially to a BoNT/A cleaved SNAP25. In some embodiments, the anti-SNAP25 antibody binds preferentially to a SNAP25 that has been cleaved by a recombinant botulinum toxin with enzymatic (light chain) activity of botulinum toxin serotype A. In other embodiments, the anti-SNAP25 antibody does not bind to full length or uncleaved SNAP25.

In other embodiments, the anti-SNAP25 antibody is able to detect BoNT/A cleaved SNAP25 (or SNAP25 cleaved by a recombinant botulinum toxin with enzymatic (light chain) activity of botulinum toxin serotype A) in a tissue. In some embodiments, the tissue is a biopsy sample. In other embodiments, the tissue is a skin punch.

In some embodiments, the anti-SNAP25 antibody comprises a light chain sequence of SEQID NO:1 or SEQID NO: 2 and is a recombinant murine antibody. In other embodiments, the anti-SNAP25 antibody comprises a heavy chain sequence of SEQID NO:3 or SEQID NO:4 and is a recombinant murine antibody. In other embodiments, the anti-SNAP25 antibody comprises a light chain sequence of SEQID NO:5 or SEQID NO: 6 and is a recombinant human antibody. In other embodiments, the anti-SNAP25 antibody comprises a heavy chain of SEQID NO:7 or SEQID NO:8 and is a recombinant human antibody. In other embodiments, the anti-SNAP25 antibody is an antibody that binds to the same epitope of an antibody with a heavy chain and/or light chain comprising one or more sequences of SEQID NOs:1-8.

The invention also encompasses a method of diagnosing if a tissue has been exposed to BoNT/A enzymatic activity comprising contacting a tissue sample suspected of having been exposed to BoNT/A enzymatic activity with an anti-SNAP25 antibody wherein the antibody preferentially binds to a BoNT/A cleaved SNAP25; and detecting whether the anti-SNAP25 antibody bound to the tissue sample, wherein the presence of the anti-SNAP25 antibody binding to the tissue sample indicates that the tissue sample has been exposed to BoNT/A enzymatic activity. In some embodiments, the BoNT/A enzymatic activity is from a native BoNT/A. In other embodiments, the BoNT/A activity is from a recombinant botulinum toxin with enzymatic (light chain) activity of botulinum toxin serotype A. In some embodiments, the anti-SNAP25 antibody used in the method comprises a light chain sequence of SEQID NO:1 or SEQID NO: 2 and is a recombinant murine antibody. In other embodiments, the anti-SNAP25 antibody used in the method comprises a heavy chain sequence of SEQID NO:3 or SEQID NO:4 and is a recombinant murine antibody. In other embodiments, the anti-SNAP25 antibody used in the method comprises a light chain sequence of SEQID NO:5 or SEQID NO: 6 and is a recombinant human antibody. In other embodiments, the anti-SNAP25 antibody used in the method comprises a heavy chain of SEQID NO:7 or SEQID NO:8 and is a recombinant human antibody. In other embodiments, the anti-SNAP25 antibody used in the method is an antibody that binds to the same epitope of an antibody with a heavy chain and/or light chain comprising one or more sequences of SEQID NOs:1-8.

In another aspect, the invention encompasses a kit for diagnosing if a tissue has been exposed to BoNT/A enzymatic activity comprising an anti-SNAP25 antibody, wherein the antibody binds preferentially to BoNT/A cleaved SNAP25. In some embodiments, the BoNT/A enzymatic activity is from a native BoNT/A. In other embodiments, the BoNT/A activity is from a recombinant botulinum toxin with enzymatic (light chain) activity of botulinum toxin serotype A. In some embodiments, the anti-SNAP25 antibody used in the kit comprises a light chain sequence of SEQID NO:1 or SEQID NO: 2 and is a recombinant murine antibody. In other embodiments, the anti-SNAP25 antibody used in the kit comprises a heavy chain sequence of SEQID NO:3 or SEQID NO:4 and is a recombinant murine antibody. In other embodiments, the anti-SNAP25 antibody used in the kit comprises a light chain sequence of SEQID NO:5 or SEQID NO: 6 and is a recombinant human antibody. In other embodiments, the anti-SNAP25 antibody used in the kit comprises a heavy chain of SEQID NO:7 or SEQID NO:8 and is a recombinant human antibody. In other embodiments, the anti-SNAP25 antibody used in the kit is an antibody that binds to the same epitope of an antibody with a heavy chain and/or light chain comprising one or more sequences of SEQID NOs:1-8.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 4(C, D) shows Western Blot analysis demonstrating the epitope specificity of Ab632-rMAb using SiMa cell lysates treated with BoNT/A ($L_3$), BoNT/C ($L_4$), BoNT/E ($L_5$) or with no toxin ($L_2$). (C) Blot probed with a commercially available anti-SNAP25 mAb (SMI-81R) that recognizes both the full-length (206) and cleaved (197 for BoNT/A, 198 for BoNT/C and 180 for BoNT/E) forms of SNAP25. In lane 2, only $SNAP25_{206}$ is detected, whereas in lane 3, both $SNAP25_{206}$ (arrow) and $SNAP25_{197}$ are detected. In lane 4, both $SNAP25_{206}$ (arrow) and $SNAP25_{198}$ are detected and in lane 5, both $SNAP25_{206}$ (arrow) and $SNAP25_{180}$ are detected; (D) Blot probed with Ab632 anti-$SNAP25_{197}$ rMAb. In lane 2, 4 and 5, no band is detected, whereas in lane 3, a single band for $SNAP25_{197}$ is detected. Lane 1, protein ladder; Lane 2, untreated SiMa cell lysate; Lane 3, BoNT/A-treated SiMa cell lysate; Lane 4, BoNT/C-treated SiMa cell lysate; Lane 5, BoNT/E-treated SiMa cell lysate.

DETAILED DESCRIPTION OF THE INVENTION

I. Definitions

Figure 1:
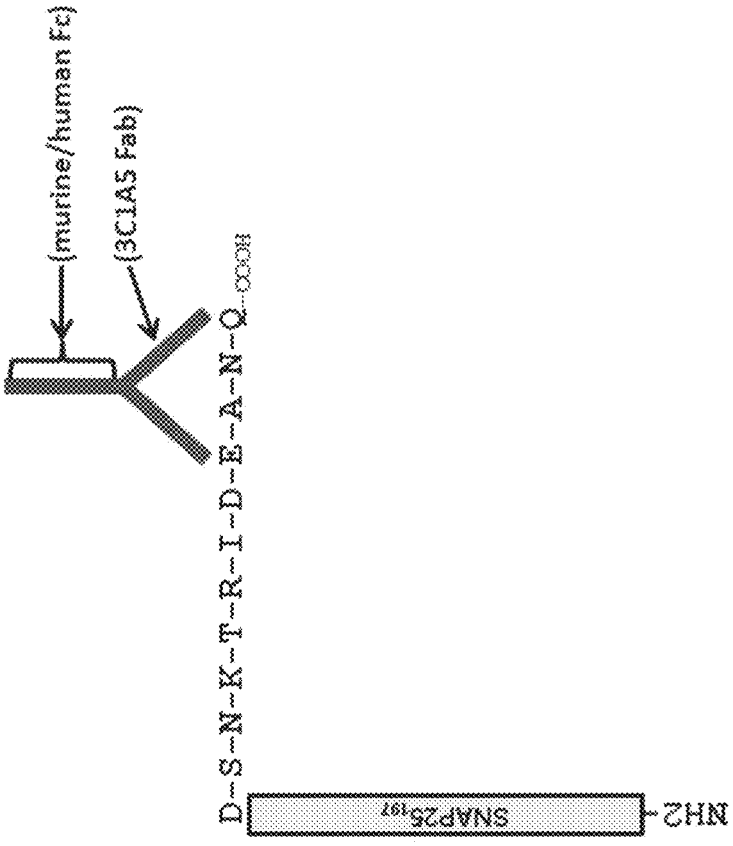
FIG. 1 shows a diagrammatic representation of the putative epitope for the humanized and murine recombinant monoclonal antibodies against $SNAP25_{197}$. The diagram shows the 12-residue peptide (SEQ ID NO. 9), minus the N-terminal cysteine residue (used for conjugation to the Keyhole Limpet Hemocyanin) that was used to generate the original monoclonal antibody.

Unless defined otherwise, all technical and scientific terms used herein have the meaning commonly understood by a person skilled in the art to which this invention belongs. As used herein, the following terms have the meanings ascribed to them unless specified otherwise.

"BoNT/A" refers to botulinum toxin serotype A produced by *Clostridium botulinum.*

"OnabotulinumtoxinA" refers to the trade name of BOTOX®, which is an FDA-approved formulation of the 900 kDa botulinum neurotoxin serotype A complex.

An epitope that "specifically binds" or "preferentially binds" (used interchangeably herein) to an antibody or a polypeptide is a term that is well understood in the art, and methods to determine such specific or preferential binding are also well known in the art. A molecule is said to exhibit "specific binding" or "preferential binding" if it reacts or associates more frequently, more rapidly, with greater duration and with greater affinity with a particular cell or substance than it does with alternative cells or substances. An antibody "specific binding" or "preferential binding" to a target if it binds with greater affinity, avidity, more readily, more exclusively and/or with greater duration than it binds to other substances. It is understood by reading this definition that, for an example, an antibody (or moiety or epitope) that specifically or preferentially binds to a first target may or may not specifically or preferentially bind to a second target. As such, “specific binding” or “preferential binding” does not necessarily require (although it can include) exclusive binding. Generally, but not necessarily, reference to binding herein means preferential binding.

“$SNAP25_{197}$” as used herein refers to the 197 amino acid fragment of synaptosomal-associated protein, 25 kDa (SNAP25) that is produced when full-length SNAP25 protein is cleaved by botulinum toxin serotype A or a recombinant botulinum toxin with enzymatic (light chain) activity of botulinum toxin serotype A.

“$SNAP25_{206}$” as used herein refers to the full length SNAP25 protein containing 206 amino acids.

It is to be understood that this invention is not limited to particularly exemplified antibodies, formulations, or methods of using such antibodies, which as such, may vary. It is also to be understood that the technical terminology used herein is for the purpose of describing particular embodiments of the invention only, and is not intended to be limiting.

II. Antibodies that Bind to $SNAP25_{197}$

BoNT/A molecular targets, including synaptic vesicle glycoprotein 2C (SV2C), fibroblast growth factor receptor 3 (FGFR3) and $SNAP25_{206}$, are broadly expressed and co-localized in autonomic and sensory nerve fibers throughout the body, including rat and primate urinary bladder and glabrous skin. Consequently, the nerve endings are likely equally susceptible to the inhibitory effects of BoNT/A. Although antibodies exist against various molecular targets of BoNT/A, there has not been an optimal antibody identified that is useful for detecting cleaved (i.e., BoNT/A activity) SNAP25 (e.g., $SNAP25_{197}$ fragment) in both Western blotting technique and also in tissue samples (e.g., using immunofluorescence).

Aspects of the present disclosure comprise, in part, an anti-SNAP25 antibody that is specific for the BoNT/A SNAP25 cleavage product that can be used in ELISA assays, Western blot applications, in cell culture assays and in tissue samples to detect BoNT/A activity. Another aspect of the present invention is an anti-SNAP25 antibody with an epitope to the carboxy terminus of the $SNAP25_{197}$ fragment that does not substantially bind to full length SNAP25 ($SNAP25_{206}$).

Methods for making antibodies (monoclonal or polyclonal) are known in the art. One method which may be employed is the method of Kohler and Milstein, Nature 256:495-497 (1975) or a modification thereof. Typically, monoclonal antibodies are developed in non-human species such as mice. In general, a mouse or rat is used for immunization but other animals may also be used. Also, once an antibody is identified to have the binding characteristics that are desired, the antigen-binding site including their complementarity determining regions (CDRs) can be fused to the constant domains or supporting framework region of antibodies of other species including human. In some instances, producing these recombinant monoclonal antibodies can minimize unwanted immunological response in patients or host animals that these antibodies are injected into. In other instances, producing these recombinant monoclonal antibodies can expand the utility of a specific antibody with certain binding characteristics for diagnostic or use for detecting BoNT/A activity in tissues of different species of animals. In some instances, recombinant monoclonal antibodies may have an advantage of minimal “off target” signal because of the selectively of not only the CDR, but also due to the recombinant IgG backbone, which can be very different than the endogenous IgG of the tissue of interest.

Anti-$SNAP25_{197}$ antibodies were generated and described in US Patent Publication No. US2012/0225436A1, hereby incorporated by reference. The CDRs of one of these monoclonal antibodies, selected for its superior performance in immunohistochemical (IHC) assays, were sequenced and recombinantly engineered into immunoglobulin backbones from either human (IgG1) or murine (IgG2A) origin. These antibodies were further characterized along with commercially available antibodies for their specificity to cleaved SNAP25 ($SNAP25_{197}$) in both Western blot assays and for use in tissue samples (either rat tissue or human tissue) using immunofluorescence. Table 1 below includes a list of anti-SNAP25 that were used in this comparison.

TABLE 1

List of anti-SNAP25 antibodies

| Antibody | Specificity | Vendor | Species/ Type | IgG-isotype | $SNAP25_{197}$ antigen |
|---|---|---|---|---|---|
| SMI-81R | $SNAP25_{206/197}$ | Covance, Princeton, NJ | Murine/ mAb | IgG1 | Uncleaved SNAP25 |
| MC-6050 | $SNAP25_{206/197}$ | R&D Abs, LV, NV | Murine/ mAb | n/a | 15-mer, $C_{OOH}$-term |
| MC-6053 | $SNAP25_{197}$ | R&D Abs, LV, NV | Murine/ mAb | n/a | 15-mer, $C_{OOH}$-term |
| Ab507 | $SNAP25_{197}$ | Allergan | Murine/ mAb | n/a | 12-mer, $C_{OOH}$-term |
| Ab632 | $SNAP25_{197}$ | Allergan | rHuman/ rMAb | IgG1 | 12-mer, $C_{OOH}$-term |
| Ab635 | $SNAP25_{197}$ | Allergan | rMurine/ rMAb | IgG2A | 12-mer, $C_{OOH}$-term |
| RGT-1092 | $SNAP25_{197}$ | Allergan | Rabbit/ pAb | IgG | 7-mer, $C_{OOH}$-term |

n/a = not available;
mAb = mouse monoclonal antibody;
rMAb = recombinant monoclonal antibody;
pAb = rabbit polyclonal antibody III. Characterization of Anti-$SNAP25_{197}$ Antibodies Several methods can be used to characterize anti-SNAP25 antibodies. One method is to identify the epitope to which it binds. Epitope mapping is commercially available from various sources, for example, Pepscan Systems (Edelhertweg 15, 8219 PH Lelystad, The Netherlands). Epitope mapping can be used to determine the sequence to which an anti-SNAP25 antibody binds. The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with anti-SNAP25 antibodies. The epitope to which anti-SNAP25 antibody binds can be determined in a systematic screening by using overlapping peptides derived from the extracellular sequence and determining binding by an anti-SNAP25 antibody.

Another method that can be used to characterize an anti-SNAP25 antibody is to use competition assays with other antibodies that bind to the same antigen or even the same epitope on the same antigen. Competition assays are well known to those skilled in the art.

Another method of characterizing anti-SNAP25 antibodies is by the antigen to which it binds. Anti-SNAP25 antibodies can be used in Western blots. Specifically, in some embodiments, anti-SNAP25 antibodies were used in Western blot assays to determine its specificity to BoNT/A cleaved SNAP25 ($SNAP25_{197}$). Anti-SNAP25 antibodies that preferentially bind to $SNAP25_{197}$ and not full-length (i.e., uncleaved) SNAP25 in Western blot assays are preferred embodiments of the present disclosure. Characterization of anti-SNAP25 antibodies in Western blot assays are detailed in the Examples below.

IV. Methods of Diagnosing BoNT/A Activity in Tissue Samples

Antibodies that binds to BoNT/A cleaved SNAP25 ($SNAP25_{197}$) may be used to identify the presence or absence of BoNT/A activity in a variety of tissues. Such tissues may include skin, including but not limited to, glabrous or hairy, muscle, including but not limited to skeletal muscle and smooth muscle, bladder, glandular tissues, including but not limited to prostate, lacrimal gland, endocrine glands, and exocrine glands, blood vessels, spinal cord and brain, including nerve fibers within any and all of these tissues. Such tissues may be procured as part of a biopsy or skin punch.

An antibody that is suitable for use to detect BoNT/A activity in tissues would need to (1) be specific to binding to $SNAP25_{197}$ and not to full-length or uncleaved SNAP 25 ($SNAP25_{206}$); and (2) be able to detect $SNAP25_{197}$ preferentially (and not full-length or uncleaved SNAP25) in tissue samples. Another characteristic that would be desirable is that the antibody would preferentially bind to BoNT/A cleaved SNAP25 ($SNAP25_{197}$) in tissue samples without substantially binding to non-specific antigens (i.e., low or no background, non-specific binding).

Determining the absence or presence of BoNT/A, or BoNT/A-like compound activity in a particular tissue sample may be important for a variety of clinical and non-clinical diagnostic purposes including, but not limited to: 1) understanding the mechanism of action for BoNT/A in a particular tissue or clinical indication; 2) assessment of BoNT/A activity and/or spread beyond the site of injection; 3) assessment of suspected immunity to BoNT/A; 4) assessment and understanding of local diffusion of BoNT/A (e.g., from an injected muscle to a neighboring muscle or tissue); 5) assessment of potential exposure to BoNT/A in the setting of human botulism performed by biopsy; and 6) clinical pharmacological studies.

In one embodiment, the use can involve the formation of a complex between $SNAP25_{197}$ and an antibody that specifically binds to $SNAP25_{197}$. In one embodiment of the diagnostic methods of this invention, the anti-$SNAP25_{197}$ antibody can bear a detectable label. Examples of labels may be used include a radioactive agent, a fluorophore, chemical label, a biological agent such as but not limited to, biotin/streptavidin detection, or an enzymatic substrate label. In other embodiments, a secondary antibody of another species that can bear a detectable label can be used to detect the anti-$SNAP25_{197}$ antibody. The use of a secondary antibody may in some cases, boost the signal of the primary anti-$SNAP25_{197}$ antibody, thereby detecting low/lower levels of BoNT/A activity in tissue samples.

V. Compositions of this Invention

This invention also encompasses compositions comprising an anti-$SNAP25_{197}$ antibody that can preferentially detect BoNT/A cleaved SNAP25 without detecting uncleaved SNAP25 ($SNAP25_{206}$) in ELISA, Western blot assays and in tissue samples. In some embodiments, the anti-$SNAP25_{197}$ antibody is a recombinant monoclonal antibody where the CDR has been fused with the supporting framework of an antibody of a different species. In other embodiments, the anti-$SNAP25_{197}$ antibody is a recombinant monoclonal antibody where the CDR has been fused with the supporting framework of an antibody of the same species. In some embodiments, the anti-$SNAP25_{197}$ antibody is a recombinant monoclonal antibody where the CDR has been fused with the supporting framework of a human antibody. In some embodiments, the anti-$SNAP25_{197}$ antibody is a recombinant monoclonal antibody where the CDR has been fused with the supporting framework of a mouse antibody.

It was found that one antibody, 3C1A5, that has been previously preliminarily described in US2012/0225436 was especially useful in the present invention because of its inherent ability to detect $SNAP25_{197}$ in BoNT/A-treated tissues. It was known that 3C1A5 preferentially bound to $SNAP25_{197}$ in an immuno-based (e.g., ELISA) assay and/or in a cell-based assay. FIG. 1 shows a depiction of the putative epitope binding site of the 3C1A5 antibody on $SNAP25_{197}$. As described in detail in the Examples, this antibody (and its recombinant human and murine versions) also preferentially detected (or bind to) BoNT/A cleaved SNAP25 ($SNAP25_{197}$) in Western blot assays. Surprisingly, this antibody (and its recombinant human and murine versions) also was able to preferentially detect (or bind to) BoNT/A cleaved SNAP25 ($SNAP25_{197}$) in rat and human tissue samples. Although there exists reports of anti-cleaved SNAP25 antibodies being able to preferentially detect (or bind to) $SNAP25_{197}$ in Western blot assays and in tissue sample, as shown in detail in the Examples, 3C1A5 (or its recombinant human and murine versions) was the only antibody that consistently detected $SNAP25_{197}$ in all assays and on different tissues and did not exhibit non-specific binding to other epitopes.

In some cases, the antibody of the present invention is 3C1A5. In other cases, the antibody of the present invention is a recombinant antibody comprising the antigen binding site of 3C1A5, but has been fused with the framework regions of another antibody from the same or different species.

In one embodiment, the light chain/heavy chain of the anti-SNAP25$_{197}$ antibody comprises one or more of the sequences listed below in Table 2.

TABLE 2

| Ab635 and 632 Antibody Sequence |
| --- |
| Murine-3C1A5 (Ab635) Sequence - (pOptiVec/pcDNA3)<br>SEQ ID NO: 1 Light Chain Murine 3C1A5 (Ab635) |
| DVVMTQTPLTLSVTIGQPASISCKSSQSLLNTNGKTYLTWLIQRPGQSPQRLIYLVSKL<br>DSGVPDRFSGSGSGTDFTLKISRVEAEDLGVYYCLQSSHFPFTFGSGTKLEIKRADAA<br>PTVSIFPPSSEQLTSGGASVVCFLNNFYPKDINVKWKIDGSERQNGVLNSWTDQDSK<br>DSTYSMSSTLTLTKDEYERHNSYTCEATHKTSTSPIVKSFNRNEC |
| SEQ ID NO: 2 Light Chain Variable Domain Murine 3C1A5<br>(Ab635) |
| DVVMTQTPLTLSVTIGQPASISCKSSQSLLNTNGKTYLTWLIQRPGQSPQRLIYLVSKL<br>DSGVPDRFSGSGSGTDFTLKISRVEAEDLGVYYCLQSSHFPFTFGSGTKLEIK |
| SEQ ID NO: 3 Heavy Chain Murine 3C1A5 (Ab635) |
| QVKLQESGAELVKPGASVKISCKASGYTFTDHSIHWVKQKPGQGLEWIGYLFPGNG<br>NFEYNEKFKGKATLTADKSSSTVYMYLNSLTSEDSAVYFCKRMGYWGQGTTVTVS<br>SAKTTPPSVYPLAPGSAAQTNSMVTLGCLVKGYFPEPVTVTWNSGSLSSGVHTFPAV<br>LESDLYTLSSSVTVPSSPRPSETVTCNVAHPASSTKVDKKIVPRDCGCKPCICTVPEVS<br>SVFIFPPKPKDVLTITLTPKVTCVVVDISKDDPEVQFSWFVDDVEVHTAQTQPREEQF<br>NSTFRSVSELPIMHQDWLNGKEFKCRVNSAAFPAPIEKTISKTKGRPKAPQVYTIPPPK<br>EQMAKDKVSLTCMITDFFPEDITVEWQWNGQPAENYKNTQPIMNTNGSYFVYSKLN<br>VQKSNWEAGNTFTCSVLHEGLHNHHTEKSLSHSPGK |
| SEQ ID NO: 4 Heavy Chain Variable Domain Murine<br>3C1A5 (Ab635) |
| QVKLQESGAELVKPGASVKISCKASGYTFTDHSIHWVKQKPGQGLEWIGYLFPGNG<br>NFEYNEKFKGKATLTADKSSSTVYMYLNSLTSEDSAVYFCKRMGYWGQGTTVTVS<br>S |
| Human-3C1A5 (Ab632) Sequence - (pOptiVec/pcDNA3)<br>SEQ ID NO: 5 Light Chain Human 3C1A5 (Ab632) |
| DVVMTQTPLTLSVTIGQPASISCKSSQSLLNTNGKTYLTWLIQRPGQSPQRLIYLVSKL<br>DSGVPDRFSGSGSGTDFTLKISRVEAEDLGVYYCLQSSHFPFTFGSGTKLEIKRTVAA<br>PSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC |
| SEQ ID NO: 6 Light Chain Variable Domain Human<br>3C1A5 (Ab632) |
| DVVMTQTPLTLSVTIGQPASISCKSSQSLLNTNGKTYLTWLIQRPGQSPQRLIYLVSKL<br>DSGVPDRFSGSGSGTDFTLKISRVEAEDLGVYYCLQSSHFPFTFGSGTKLEIK |
| SEQ ID NO: 7 Heavy Chain Human 3C1A5 (Ab632) |
| QVKLQESGAELVKPGASVKISCKASGYTFTDHSIHWVKQKPGQGLEWIGYLFPGNG<br>NFEYNEKFKGKATLTADKSSSTVYMYLNSLTSEDSAVYFCKRMGYWGQGTTVTVS<br>SASTKGPSVFPLAPSSKSTSGGTAALGCLVKDYFPEPVTVSWNSGALTSGVHTFPAVL<br>QSSGLYSLSSVVTVPSSSLGTQTYICNVNHKPSNTKVDKKVEPKSCDKTHTCPPCPAP<br>ELLGGPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| SEQ ID NO: 8 Heavy Chain Variable Domain Human<br>3C1A5 (Ab632) |
| QVKLQESGAELVKPGASVKISCKASGYTFTDHSIHWVKQKPGQGLEWIGYLFPGNG<br>NFEYNEKFKGKATLTADKSSSTVYMYLNSLTSEDSAVYFCKRMGYWGQGTTVTVS<br>S |

In some cases, the antibodies of the invention comprises a light chain sequence of SEQID NO:1 or SEQ ID NO:2 and is a recombinant murine antibody. In other cases, the antibodies of the invention comprises a heavy chain sequence of SEQID NO:3 or SEQID NO:4 and is a recombinant murine antibody. In other cases, the antibodies of the invention comprises a light chain sequence of SEQID NO: 5 or SEQID NO: 6 and is a recombinant human antibody. In other cases, the antibodies of the invention comprises a heavy chain sequence of SEQID NO:7 or SEQID NO:8 and is a recombinant human antibody.

Still in other embodiments the antibodies of the invention can be an antibody that binds to the same epitope of an antibody with a heavy chain and/or light chain comprising one or more sequences of SEQID NOs:1-8. In some cases, the antibodies of the invention can be an antibody that will compete for binding to the same epitope of an antibody with a heavy chain and/or light chain comprising one or more sequences of SEQID NOs:1-8.

The following Examples are provided to illustrate, but not to limit the invention.

IV. Examples

Example 1. Western Blot Comparison

SNAP25 antibodies (listed in Table 1) were first compared by Western blot analysis in their ability to recognize the full-length (206) or BoNT/A-cleaved (197) forms of SNAP25 from rat embryonic cortical cell lysates and in SiMa cell lysates treated with and without BoNT/A. (See FIGS. 2 and 3).

Rat cortical neurons were harvested from embryonic pups (E18) and digested in a papain dissociation system (Worthington Biochemical Corp., Lakewood, N.J.) at 37° C. for 15 minutes to obtain individual cells. Cortical cells were then transferred to Neurobasal medium (Life Technologies, Carlsbad, Calif.) containing B-27 supplements, 0.5 mM L-glutamine and penicillin/streptomycin. Rat dorsal root ganglia (DRG) harvested from neonatal pups (P7-P14) were pooled and digested in papain-containing HBSS (final concentration of 20 units of papain per ml in 1 mM L-cysteine) at 37° C. for 15 minutes. Ganglia were washed and subsequently digested in Ca2+/Mg2+-free HBSS containing Type 1 collagenase (1.7 mg/ml, Sigma, St Louis, Mo.) and incubated at 37° C. for an additional 15 minutes. The ganglia were then washed in Neurobasal-A media (Life Technologies, Carlsbad, Calif.) containing B-27 supplements, 0.5 mM L-glutamine, penicillin/streptomycin and 20 ng/ml 2.5S nerve growth factor (NGF) and gently triturated through Pasteur pipettes. Cortical and DRG cells were homogenously dispersed, plated onto poly-D-lysine/laminin-coated 12-mm coverslips (BD Biosciences, San Jose, Calif.) placed in 100-mm culture dishes and grown for 6 to 7-DIV prior to treatment. All animal protocols and procedures were approved by the Allergan Institutional Animal Care and Use Committee and performed in accordance with NIH guidelines.

On select days, cultures were treated with or without 3 nM BoNT/A (150 kDa; Metabiologics, Madison, Wis.) for 3 hr at 37° C. Following treatment, cells were rinsed with and then incubated in fresh culture medium overnight. Cortical cells were then washed with PBS, lysed in freshly prepared Lysis Buffer (20 mM Tris pH 7.5, 0.15 M sodium chloride, 1 nM EDTA, 1 mM EGTA, 10% Triton X-100 and one tablet of EDTA-free protease inhibitors) for 20 min on ice and then centrifuged at 4000 rpm for 20 min to eliminate debris prior to Western blot (WB) analysis. DRG cells were washed, fixed with 4% paraformaldehyde for 10-15 min and processed for immunocytochemistry according to the protocol below.

SiMa cells (DSMZ, Germany) were cultured in BD Biosciences brand Collagen IV flasks (VWR, Radnor, Pa.) with vented caps (Marini, P., MacLeod, R. A., Treuner, C., Bruchelt, G., Bohm, W., Wolburg, H., Schweizer, P., and Girgert, R., 1999. SiMa, a new neuroblastoma cell line combining poor prognostic cytogenetic markers with high adrenergic differentiation. Cancer Genet. Cytogenet. 112, 161-164.). Growth media consisted of RPMI 1640, 0.1 mM Non-Essential Amino-Acids, 10 mM HEPES, 1 mM Sodium Pyruvate, 100 U/mL Penicillin, 100 μg/mL Streptomycin, and 10% Fetal Bovine Serum. Cells were treated with or without BoNT/A (0.01 nM) for 24 hrs at 37° C. Following treatment, SiMa cells were washed with PBS, lysed in freshly prepared Lysis Buffer for 20 min on ice and then centrifuged at 4000 rpm for 20 min to eliminate debris prior to WB analysis.

For WB assays, we employed rat embryonic cortical neurons as well as a human neuroblastoma cell line (SiMa), which is known for its sensitivity to BoNT/A-mediated SNAP25 cleavage (Fernandez-Salas, E., Wang, J., Molina, Y., Nelson, J. B., Jacky, B. P., and Aoki, K. R., 2012. Botulinum neurotoxin serotype A specific cell-based potency assay to replace the mouse bioassay. PLoS. One. 7, e49516.). Total cell lysates from these cultures were separated by electrophoresis (Biorad TGX Any Kd gel) and the gel was transferred onto a PVDF membrane. Blots were blocked in buffer (5% dry milk in 1×TBS-0.1% Tween-20) for 1 hr at room temperature and then incubated overnight at 4° C. with primary antibodies in blocking buffer. Following washes, blots were incubated with HRP-conjugated secondary antibodies (Bio Rad, Hercules, Calif.) and developed by ECL Plus (GE Healthcare, Pittsburgh, Pa.). A separate control blot was probed for glyceraldehyde 3-phosphate dehydrogenase (GAPDH) to show equal loading of cell lysate samples. Western blots were scanned using a variable mode GE Typhoon 9410 imager and analyzed with ImageQuant TL v.2005 software (GE Healthcare, Pittsburgh, Pa.).

First a commercially available and widely-used monoclonal antibody (SMI-81R) directed against all forms of the SNAP25 protein recognized both $SNAP25_{206}$ and $SNAP25_{197}$ (FIG. 2A). In contrast, a second commercially available monoclonal antibody (MC-6050) described as recognizing both forms of SNAP25 was surprisingly specific for $SNAP25_{197}$ in lysates from toxin-treated cells (FIG. 2B). Furthermore, another antibody from the same company (MC-6053), described as recognizing only BoNT/A-cleaved SNAP25 revealed a thin, faint band exclusively in the toxin-treated lane (FIG. 2C).

The human (Ab632) and murine (Ab635) rMAbs directed against BoNT/A-cleaved SNAP25 were very specific for $SNAP25_{197}$; only a single band was detected in toxin-treated lysates, while no bands were detected in the untreated, control lanes (FIG. 2D, E). Similarly, our in-house rabbit pAb (RGT-1092) against $SNAP25_{197}$ only detected a band in the BoNT/A-treated sample, while no bands were detected in the control lane (FIG. 2F). It was noted however, that the pAb recognized two additional faint bands, one just above the $SNAP25_{197}$ band and another at ~20 kDa present only in toxin-treated samples, which could not be readily explained. Nevertheless, the upper band is not likely to be intact SNAP25, as no band was observed in the untreated lane. Similar WB results were obtained using lysates from BoNT/A-treated and untreated SiMa cell cultures (FIG. 3), except that no band was observed for MC-6053 in either control or toxin-treated lanes (FIG. 3C). Control blots probed for GAPDH showed equal loading of all samples for both cortical and SiMa cell lysate experiments (FIG. 4A, B).

A separate WB analysis was performed to examine the epitope specificity of our rMAbs using BoNT/C- and BoNT/E-treated SiMa cell lysates compared to the BoNT/A-treated lysate. It is well established that BoNT/C cleaves SNAP25 at amino acid (aa) residue 198, while BoNT/E cleaves SNAP25 at aa residue 180 [11]. While the SMI-81R mAb recognized both full length and BoNT-cleaved forms of SNAP25 (FIG. 4C), our human rMAb only detected a single band in the BoNT/A-treated lysate sample, as expected (FIG. 4D).

Figure 2:
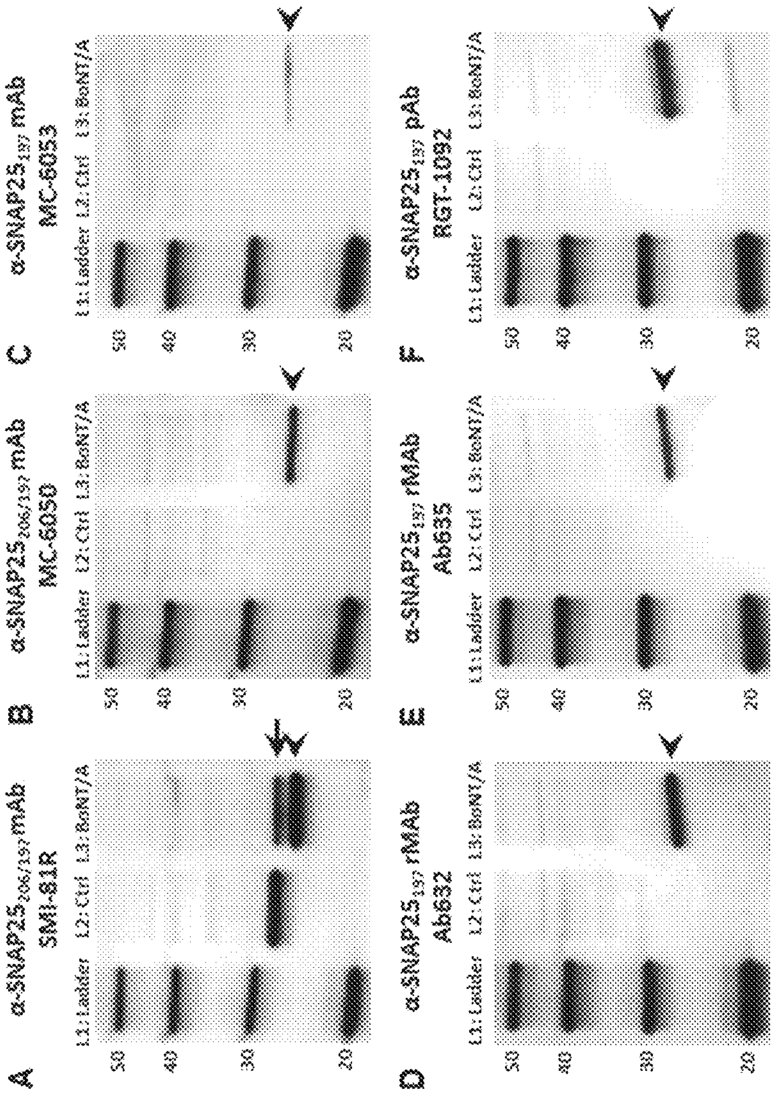
FIG. 2 (A-F) shows Western Blot analysis comparing the specificity of different antibodies for detecting full-length $SNAP25_{206}$ and cleaved $SNAP25_{197}$ in rat embryonic cortical cell lysates treated with ($L_3$) or without ($L_2$) BoNT/A at 3 nM concentration. (A) Blot probed with a commercially available anti-SNAP25 mAb (SMI-81R) that recognizes both the full-length (206) and cleaved (197) forms of SNAP25. In lane 2, only $SNAP25_{206}$ is detected, whereas in lane 3, both $SNAP25_{206}$ (arrow) and $SNAP25_{197}$ (arrowhead) are detected. (B) Blot probed with a commercially available anti-SNAP25 mAb (MC-6050) that reportedly recognizes both $SNAP25_{206}$ and $SNAP25_{197}$. Only $SNAP25_{197}$ appears as a single band in lane 3 (arrowhead). (C) Blot probed with a commercially available anti-SNAP25 mAb (MC-6053) that is reportedly specific for $SNAP25_{197}$. This antibody recognizes a thin, faint $SNAP25_{197}$ band in lane 3. (D) Blot probed with Ab632 anti-$SNAP25_{197}$ rMAb. In lane 2, no band is detected, whereas in lane 3, a single band for $SNAP25_{197}$ is detected (arrowhead). (E) Blot probed with Ab635 anti-$SNAP25_{197}$ rMAb. In lane 2, no band is detected, whereas in lane 3, a single band for $SNAP25_{197}$ is detected (arrowhead). (F) Blot probed with RGT-1092 anti-$SNAP25_{197}$ pAb. This antibody primarily recognizes $SNAP25_{197}$ in lane 3 (arrowhead), although two faint bands are visible just above and below the $SNAP25_{197}$ band. Lane 1, protein ladder; Lane 2, untreated cortical cell lysate; Lane 3, BoNT/A-treated (3 nM) cortical cell lysate.
Figure 3:
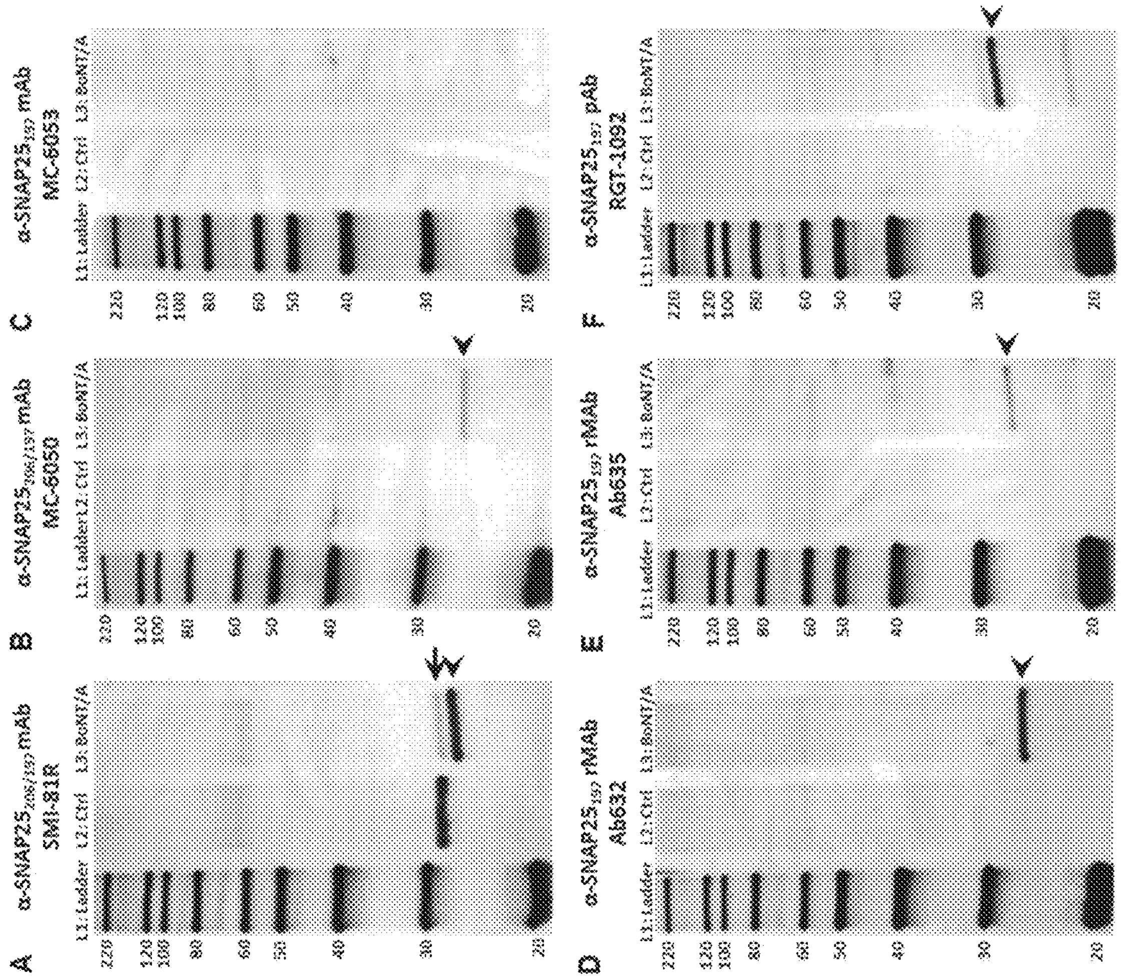
FIG. 3 (A-F) shows Western Blot analysis comparing the specificity of different antibodies for detecting full-length $SNAP25_{206}$ and cleaved $SNAP25_{197}$ in SiMa cell lysates treated with ($L_3$) or without ($L_2$) BoNT/A at 3 nM concentration. (A) Blot probed with a commercially available anti-SNAP25 mAb (SMI-81R) that recognizes both the full-length (206) and cleaved (197) forms of SNAP25. In lane 2, only $SNAP25_{206}$ is detected, whereas in lane 3, both $SNAP25_{206}$ (arrow) and $SNAP25_{197}$ (arrowhead) are detected. (B) Blot probed with a commercially available anti-SNAP25 mAb (MC-6050) that reportedly recognizes both $SNAP25_{206}$ and $SNAP25_{197}$. Only $SNAP25_{197}$ appears as a single band in lane 3 (arrowhead). (C) Blot probed with a commercially available anti-SNAP25 mAb (MC-6053) that is reportedly specific for $SNAP25_{197}$. The antibody does not appear to recognize any bands. (D) Blot probed with Ab632 anti-$SNAP25_{197}$ rMAb. In lane 2, no band is detected, whereas in lane 3, a single band for $SNAP25_{197}$ is detected (arrowhead). (E) Blot probed with Ab635 anti-$SNAP25_{197}$ rMAb. In lane 2, no band is detected, whereas in lane 3, a single band for $SNAP25_{197}$ is detected (arrowhead). (F) Blot probed with RGT-1092 anti-$SNAP25_{197}$ pAb. This antibody primarily recognizes $SNAP25_{197}$ in lane 3 (arrowhead), although two faint bands are visible just above and below the $SNAP25_{197}$ band. Lane 1, protein ladder; Lane 2, untreated SiMa cell lysate; Lane 3, BoNT/A-treated (0.01 nM) SiMa cell lysate.

FIG. 2 shows WB analysis comparing the specificity of antibodies against SNAP25 using rat embryonic cortical neuronal cell lysates treated with (L3) or without (L2) BoNT/A. (A) Blot probed with a commercially available anti-SNAP25 mAb (SMI-81R) that recognizes both the full-length (206) and cleaved (197) forms of SNAP25. In lane 2, only SNAP25206 is detected, whereas in lane 3, both SNAP25206 (arrow) and SNAP25197 (arrowhead) are detected. (B) Blot probed with a commercially available anti-SNAP25 mAb (MC-6050) that reportedly recognizes both SNAP25206 and SNAP25197. Only SNAP25197 appears as a single band in lane 3 (arrowhead). (C) Blot probed with a commercially available anti-SNAP25 mAb (MC-6053) that is reportedly specific for SNAP25197. This antibody recognizes a thin, faint SNAP25197 band in lane 3. (D) Blot probed with Ab632 anti-SNAP25197 rMAb. In lane 2, no band is detected, whereas in lane 3, a single band for SNAP25197 is detected (arrowhead). (E) Blot probed with Ab635 anti-SNAP25197 rMAb. In lane 2, no band is detected, whereas in lane 3, a single band for SNAP25197 is detected (arrowhead). (F) Blot probed with RGT-1092 anti-SNAP25197 pAb. This antibody primarily recognizes SNAP25197 in lane 3 (arrowhead), although two faint bands are visible just above and below the SNAP25197 band. Lane 1, protein ladder; Lane 2, untreated cortical cell lysate; Lane 3, BoNT/A-treated (3 nM) cortical cell lysate.

FIG. 3 shows WB analysis comparing the specificity of antibodies against SNAP25 using SiMa cell lysates treated with (L3) or without (L2) BoNT/A. (A) Blot probed with a commercially available anti-SNAP25 mAb (SMI-81R) that recognizes both the full-length (206) and cleaved (197) forms of SNAP25. In lane 2, only SNAP25206 is detected, whereas in lane 3, both SNAP25206 (arrow) and SNAP25197 (arrowhead) are detected. (B) Blot probed with a commercially available anti-SNAP25 mAb (MC-6050) that reportedly recognizes both SNAP25206 and SNAP25197. Only SNAP25197 appears as a single band in lane 3 (arrowhead). (C) Blot probed with a commercially available anti-SNAP25 mAb (MC-6053) that is reportedly specific for SNAP25197. The antibody does not appear to recognize any bands. (D) Blot probed with Ab632 anti-SNAP25197 rMAb. In lane 2, no band is detected, whereas in lane 3, a single band for SNAP25197 is detected (arrowhead). (E) Blot probed with Ab635 anti-SNAP25197 rMAb. In lane 2, no band is detected, whereas in lane 3, a single band for SNAP25197 is detected (arrowhead). (F) Blot probed with RGT-1092 anti-SNAP25197 pAb. This antibody primarily recognizes SNAP25197 in lane 3 (arrowhead), although two faint bands are visible just above and below the SNAP25197 band. Lane 1, protein ladder; Lane 2, untreated SiMa cell lysate; Lane 3, BoNT/A-treated (0.01 nM) SiMa cell lysate.

Figure 4:
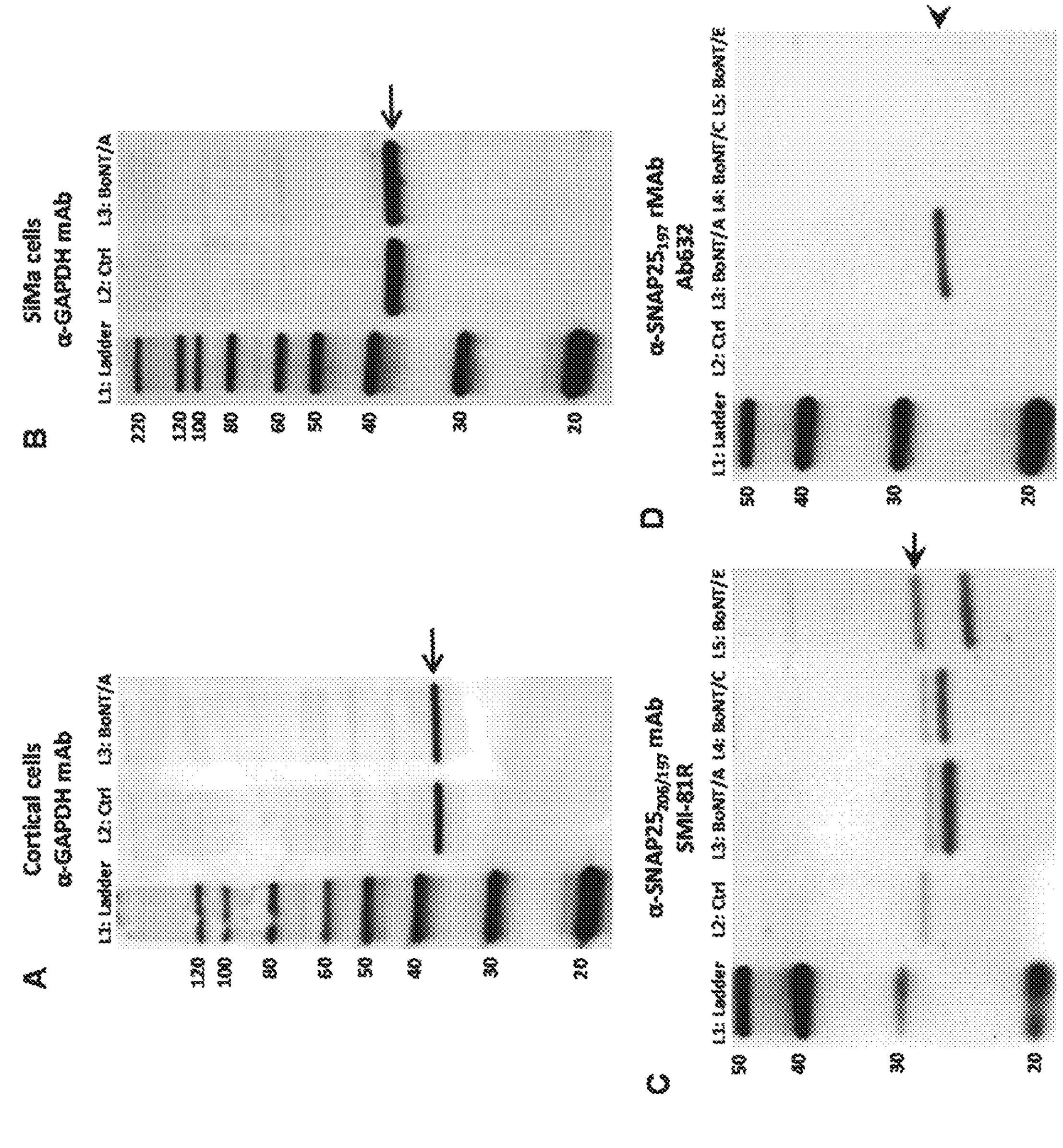
FIG. 4(A, B) shows control Western Blot analysis for the cortical cell studies in FIG. 2 and SiMa cell studies in FIG. 3 probed with anti-GAPDH mAb demonstrating equal loading of samples in lanes 2 and 3. Lane 1, protein ladder; Lane 2, untreated cell lysate; Lane 3, BoNT/A-treated (3 nM) cortical cell lysate and (0.01 nM) SiMa cell lysate.

FIG. 4(A, B) shows control blots for the cortical cell studies in FIG. 2 and SiMa cell studies in FIG. 3 probed with anti-GAPDH mAb showing equal loading of samples in lanes 2 and 3. Lane 1, protein ladder; Lane 2, untreated cell lysate; Lane 3, BoNT/A-treated (3 nM) cortical cell lysate and (0.01 nM) SiMa cell lysate. FIG. 4(C, D) shows Western Blot analysis demonstrating the epitope specificity of Ab632-rMAb using SiMa cell lysates treated with BoNT/A ($L_3$), BoNT/C ($L_4$), BoNT/E ($L_5$) or with no toxin ($L_2$). (C) Blot probed with a commercially available anti-SNAP25 mAb (SMI-81R) that recognizes both the full-length (206) and cleaved (197 for BoNT/A, 198 for BoNT/C and 180 for BoNT/E) forms of SNAP25. In lane 2, only $SNAP25_{206}$ is detected, whereas in lane 3, both $SNAP25_{206}$ (arrow) and $SNAP25_{197}$ are detected. In lane 4, both $SNAP25_{206}$ (arrow) and $SNAP25_{198}$ are detected and in lane 5, both $SNAP25_{206}$ (arrow) and $SNAP25_{180}$ are detected; (D) Blot probed with Ab632 anti-$SNAP25_{197}$ rMAb. In lane 2, 4 and 5, no band is detected, whereas in lane 3, a single band for $SNAP25_{197}$ is detected. Lane 1, protein ladder; Lane 2, untreated SiMa cell lysate; Lane 3, BoNT/A-treated SiMa cell lysate; Lane 4, BoNT/C-treated SiMa cell lysate; Lane 5, BoNT/E-treated SiMa cell lysate.

Example 2. Immunohistochemical Comparison—Rat Tissue

The specificity of the antibodies was then tested using immunohistochemistry (IHC) in rat bladder and glabrous skin that had been treated with either onabotulinumtoxinA or saline and then harvested 2-days post-injection. Throughout these IHC studies, adjacent sections processed without primary antibodies showed only background staining (data not shown).

Male Sprague-Dawley rats (Charles River Laboratories, Wilmington, Mass.) were used for this study. Rats were pair-housed in the RD3 vivarium with free access to food and water on a 12 hour light-dark cycle. All procedures were approved by the Allergan Institutional Animal Care and Use Committee and adhered to NIH guidelines.

Working solutions of onabotulinumtoxinA (BOTOX®, Allergan, Inc., Irvine, Calif.) and BoNT/A (150 kDa; Metabiologics, Madison, Wis.) were prepared in either 0.9% saline or 0.5% BSA/0.9% saline, respectively. For bladder injections, rats were first anesthetized and prepped for surgery. A lower midline abdominal incision was made, exposing the urinary bladder, seminal vesicles, and prostate gland. The urinary bladder wall was then injected at four equidistant sites along the midline circumference with 10 μl of onabotulinumtoxinA (2.5 U/kg) yielding a final toxin load of 10 U/kg. Control animals received 10 μl injections of vehicle (0.9% saline) into comparable target sites. For glabrous skin injections, onabotulinumtoxinA (30 U/kg) or vehicle was administered as a single intradermal (ID) injection (25 μl) into the center of the right hindlimb paw between the footpads.

Rats were sacrificed at 2-days post-injection and bladders or the central portion of the planter surface of the hindpaws were harvested and fixed overnight at 4° C. in Zamboni's fixative (American MasterTech, Lodi, Calif.). Tissues were washed and cryoprotected in 30% sucrose/PBS solution overnight at 4° C. Bladder and skin samples were hemisected along the midline, embedded in O.C.T. (Tissue-Tek) and stored frozen at −80° C. until sectioning. Tissue blocks were cryostat-sectioned (14 μm-thick), slide-mounted and slides were kept at −20° C. until use.

Slide-mounted tissue sections and cell culture coverslips were first blocked for non-specific signal in blocking buffer (1×PBS+0.1% Triton X-100+10% Normal Donkey Serum) and then incubated with primary antibodies at the desired concentrations in blocking buffer overnight at 4° C. Following several washes, sections and coverslips were incubated with secondary antibodies (Jackson ImmunoResearch, West Grove, Pa.) diluted in blocking buffer for 2 hr at 4° C. and then washed again. Coverslips with cultures were inverted and mounted onto microscope slides using Fluoromount-G (EM Sciences, Hatfield, Pa.) containing 1.5 μg/ml DAPI. Slide-mounted sections were coversliped using the same mounting media. Adjacent sections processed without primary antibodies served as negative controls to show background signal. Alternate sections were stained with hematoxylin & eosin for better anatomical identification.

Images were captured and analyzed using either a Zeiss LSM-710 confocal microscope with ZEN software (Carl Zeiss, Thornwood, N.Y.) or an Olympus FV1000 confocal microscope (Olympus, Center Valley, Pa.). Imaris® (Bitplane, South Windsor, Conn.) software was utilized for qualitative analysis of nerve fibers. Nerve fiber-types were identified on the basis of their morphology and neurochemistry.

In the rat bladder, the SMI-81R antibody directed against SNAP25 showed IR-signal in nerve fibers throughout the detrusor muscle. The SNAP25-IR pattern was identical in both onabotulinumtoxinA and saline-treated bladders, as expected (FIG. 5A, F). The MC-6050 monoclonal antibody, which is reported to recognize both intact and BoNT/A-cleaved forms of SNAP25, demonstrated IR-signal in nerve fibers from the detrusor muscle of toxin-treated, but not saline-treated bladder (FIG. 5B, G), comparable to the results from the Western Blot analysis. Likewise, the MC-6053 monoclonal antibody demonstrated IR-signal only in toxin-treated, but not saline-treated bladder (FIG. 5C, H). In contrast with the specificity detected in the WB analysis, RGT-1092 pAb generated against $SNAP25_{197}$ demonstrated IR-signal in both toxin-treated and saline-treated bladders (FIG. 5E, J). Most importantly, Ab632-rMAb showed clear IR-signal in nerve fibers from the detrusor muscle of toxin-treated bladders (FIG. 5D), while no signal was detected in saline-treated control bladders (FIG. 51). Moreover, in separate studies, Ab635-rMAb showed similar specificity as Ab632-rMAb to $SNAP25_{197}$ in rat bladder (FIG. 8M, R)).

In the rat glabrous skin, the SMI-81R antibody exhibited IR-signal in nerve fibers surrounding blood vessels (among other skin regions). As expected for this antibody, the SNAP25-IR pattern was identical in both onabotulinumtoxinA and saline-treated skin (FIG. 6A, F). The MC-6050 monoclonal antibody demonstrated IR-signal primarily in nerve fibers from toxin-treated skin. However, slight IR-signal was also evident in nerve fibers from saline-treated skin (FIG. 6B, G). The MC-6050 antibody also showed strong IR-signal in the lumen of blood vessels (FIG. 6B, G). But as this particular IR-signal was never demonstrated by other SNAP25 antibodies, it was determined to be non-specific. Similarly, the MC-6053 monoclonal antibody showed IR-specific signal in nerve fibers surrounding blood vessels from both toxin and saline-treated skin, as well as non-specific signal in the lumen of blood vessels (FIG. 6C, H). Once again, RGT-1092 pAb generated against $SNAP25_{197}$ demonstrated IR-signal in both toxin-treated and saline-treated rat skin (FIG. 6E, J), suggesting that despite its specificity in WB analysis, this antibody is not amenable for IHC. In clear contrast, Ab632-rMAb exhibited IR-signal in nerve fibers only in toxin-treated, but not in saline-treated skin (FIG. 6D, I) supporting its superb specificity.

Figure 7:
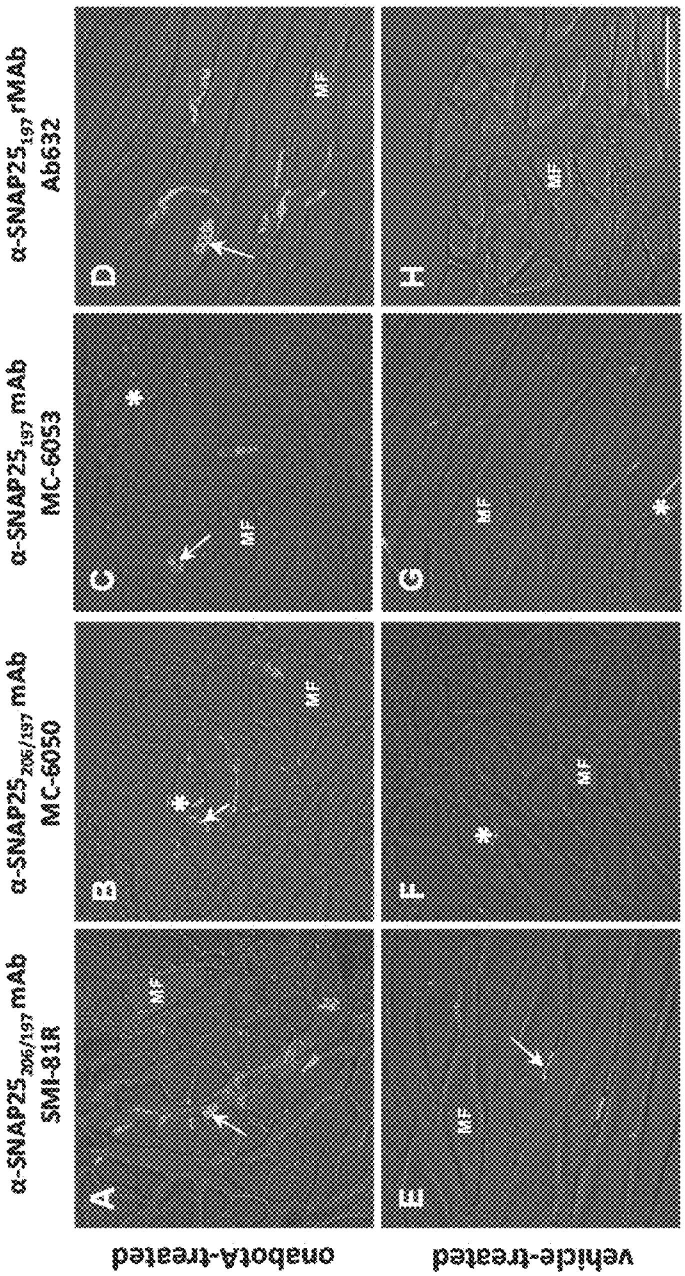
FIG. 7 (A-H) shows immunohistochemical analysis comparing the specificity of antibodies against SNAP25 in skeletal muscle underlying rat glabrous skin following treatment with either onabotulinumtoxinA (30 U/kg) or vehicle. (A-D) Confocal images showing motor nerve terminals (MNT, arrows) within the underlying muscle of the rat paw injected with onabotulinumtoxinA and probed with (A) commercial mAb (SMI-81R) against full-length (206) and cleaved (197) SNAP25; (B) a second commercial mAb (MC-6050) against $SNAP25_{197}$ & $SNAP25_{206}$; (C) a commercial mAb (MC-6053) against $SNAP25_{197}$ and (D) Ab632-rMAb against $SNAP25_{197}$; (E-H) Confocal images from control rat paw injected with vehicle and probed with the same four antibodies. SNAP25-IR signal is in green (shown as gray in black and white drawings) and DIC illumination was used to delineate the underlying muscle fibers (MF). Arrow (E) points to IR-signal within a MNT from vehicle treated rat paw; asterisks (B, C, F and G) point to non-specific IR-signal within the muscle. Scale bar=50 μm.

Our samples of rat glabrous skin often contain underlying skeletal muscle, providing an excellent opportunity to validate our rMAbs on their ability to recognize BoNT/A-cleaved SNAP25 within motor nerve terminals (MNT). Similar results for antibody specificity were observed in MNTs as in other skin nerve fiber-types (FIG. 7). While the SMI-81R mAb recognized both full length and BoNT/A-cleaved forms of SNAP25 in MNTs and axons, the commercial mAbs, MC-6050 and MC-6053 demonstrated IR-signal primarily in nerve fibers from toxin-treated skin. However, non-specific IR-signal was also observed in saline-treated tissue for these commercial mAbs (FIG. 7F, G). In contrast, Ab632-rMAb exhibited IR-signal in MNTs and axons only in toxin-treated, but not in saline-treated skin (FIG. 7D, H).

To further exemplify the Ab632-rMAb's superior specificity for $SNAP25_{197}$ in tissues, we compared the immunoreactive signal of Ab632 and Ab635 to an initial batch lot of the human rMAb (May 2, 2011), the original, native 3C1A5 mAb purified from ascites and the 2E2A6 (Ab507) mAb used for Allergan's cell-based potency assay for BOTOX® (Fernandez-Salas, E., Wang, J., Molina, Y., Nelson, J. B., Jacky, B. P., and Aoki, K. R., 2012. Botulinum neurotoxin serotype A specific cell-based potency assay to replace the mouse bioassay. PLoS. One. 7, e49516.). The IR signal for these antibodies was compared in rat glabrous skin and bladder tissues following treatment with onabotulinumtoxinA.

In rat glabrous skin, both Ab632 and Ab635 showed strong IR-signal for $SNAP25_{197}$ in nerve fibers surrounding blood vessels (FIG. 8B, C) and other areas (data not shown) following BOTOX® treatment, but this IR-signal was absent in nerve fibers from vehicle-treated controls (FIG. 8G, H). Similarly, an older and less refined batch lot of the human rMAb showed good IR-signal in skin nerve fibers following toxin treatment (FIG. 8A), but not in saline-treated controls (FIG. 8F). In contrast, no specific IR-signal for $SNAP25_{197}$ was detected in toxin-treated skin nerve fibers using either the native 3C1A5 mAb or the Ab507 mAb (FIG. 8D, E).

Comparable results were demonstrated in the rat bladder following BOTOX® treatment. All three rMAbs (Ab632, Ab635 and the older human batch lot) showed specific IR-signal for $SNAP25_{197}$ in nerve fibers throughout the detrusor muscle of the bladder (FIG. 8K, L, M). Specific IR-signal was also observed in rat bladder nerve fibers with the native 3C1A5 mAb (FIG. 8O). However, as in the rat glabrous skin, no specific $SNAP25_{197}$ IR-signal was detected in toxin-treated bladders using the Ab507 mAb (FIG. 8N), which is used in Allergan's cell-based potency assay for BOTOX®. No IR-signal was detected in vehicle-treated control rat bladders with any of the antibodies utilized (FIG. 8P-T).

Figure 5:
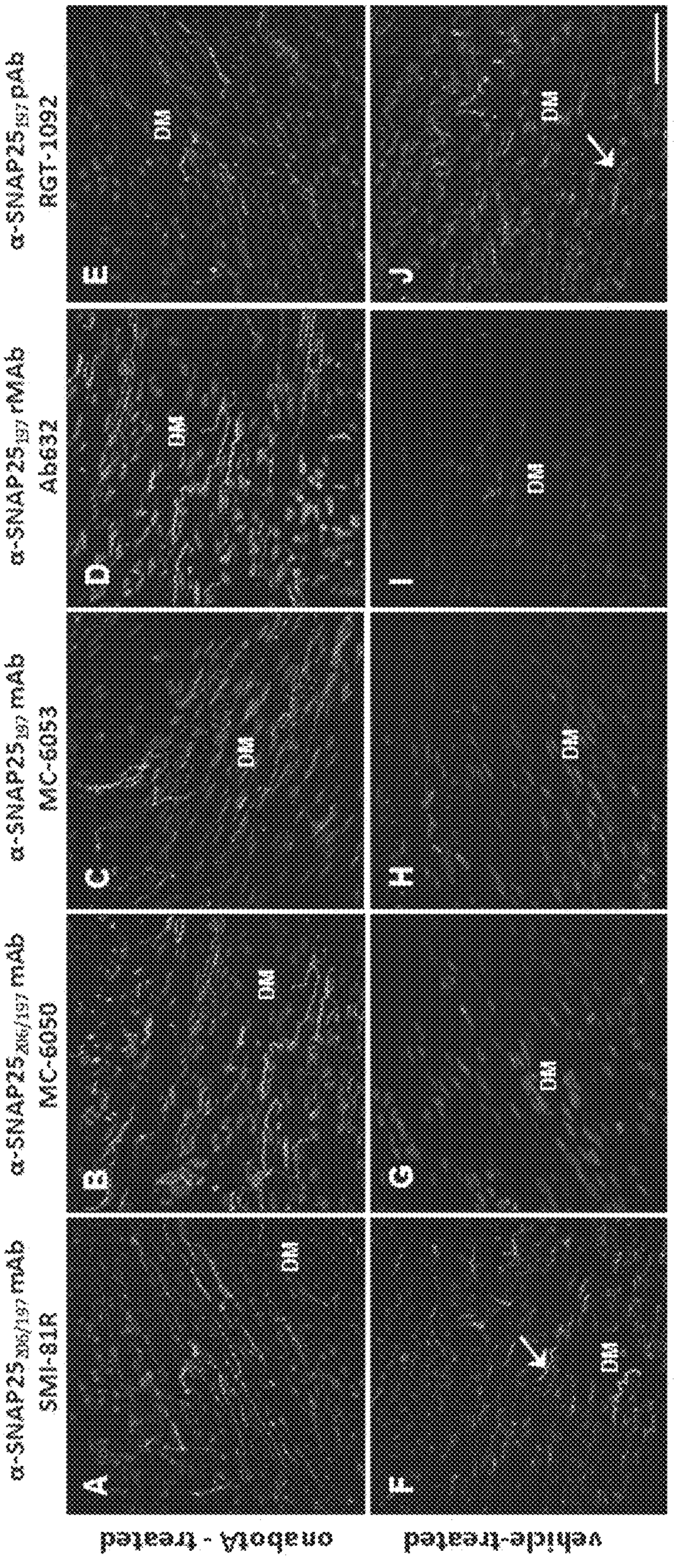
FIG. 5 (A-J) shows immunohistochemical analysis comparing the specificity of antibodies against SNAP25 in sections of rat bladder following treatment with either onabotulinumtoxinA (10 U/kg) or vehicle. (A-E) Confocal images of bladder detrusor muscle (DM) injected with onabotulinumtoxinA and probed with (A) commercial mAb (SMI-81R) against full-length (206) and cleaved (197) SNAP25, (B) a second commercial mAb (MC-6050) against $SNAP25_{197}$ & $SNAP25_{206}$, (C) commercial mAb (MC-6053) against $SNAP25_{197}$, (D) Ab632-rMAb against $SNAP25_{197}$ and (E) RGT-1092 pAb against $SNAP25_{197}$. (F-J) Confocal images of control rat bladder injected with vehicle and probed with the same five antibodies. Arrows (F and J) point to IR-signal within nerve fibers from vehicle treated rat bladder. DM, detrusor muscle; Scale bar=50 μm.

FIG. 5 shows immunohistochemical analysis comparing the specificity of antibodies against SNAP25 in sections of rat bladder following treatment with either onabotulinumtoxinA (10 U/kg) or vehicle. (A-E) Confocal images of bladder detrusor muscle (DM) injected with onabotulinumtoxinA and probed with (A) commercial mAb (SMI-81R) against full-length (206) and cleaved (197) SNAP25, (B) a second commercial mAb (MC-6050) against $SNAP25_{197}$ & $SNAP25_{206}$, (C) commercial mAb (MC-6053) against $SNAP25_{197}$, (D) Ab632-rMAb against $SNAP25_{197}$ and (E) RGT-1092 pAb against $SNAP25_{197}$. (F-J) Confocal images of control rat bladder injected with vehicle and probed with the same five antibodies. Arrows (F and J) point to IR-signal within nerve fibers from vehicle treated rat bladder. DM, detrusor muscle; Scale bar=50 μm.

Figure 6:
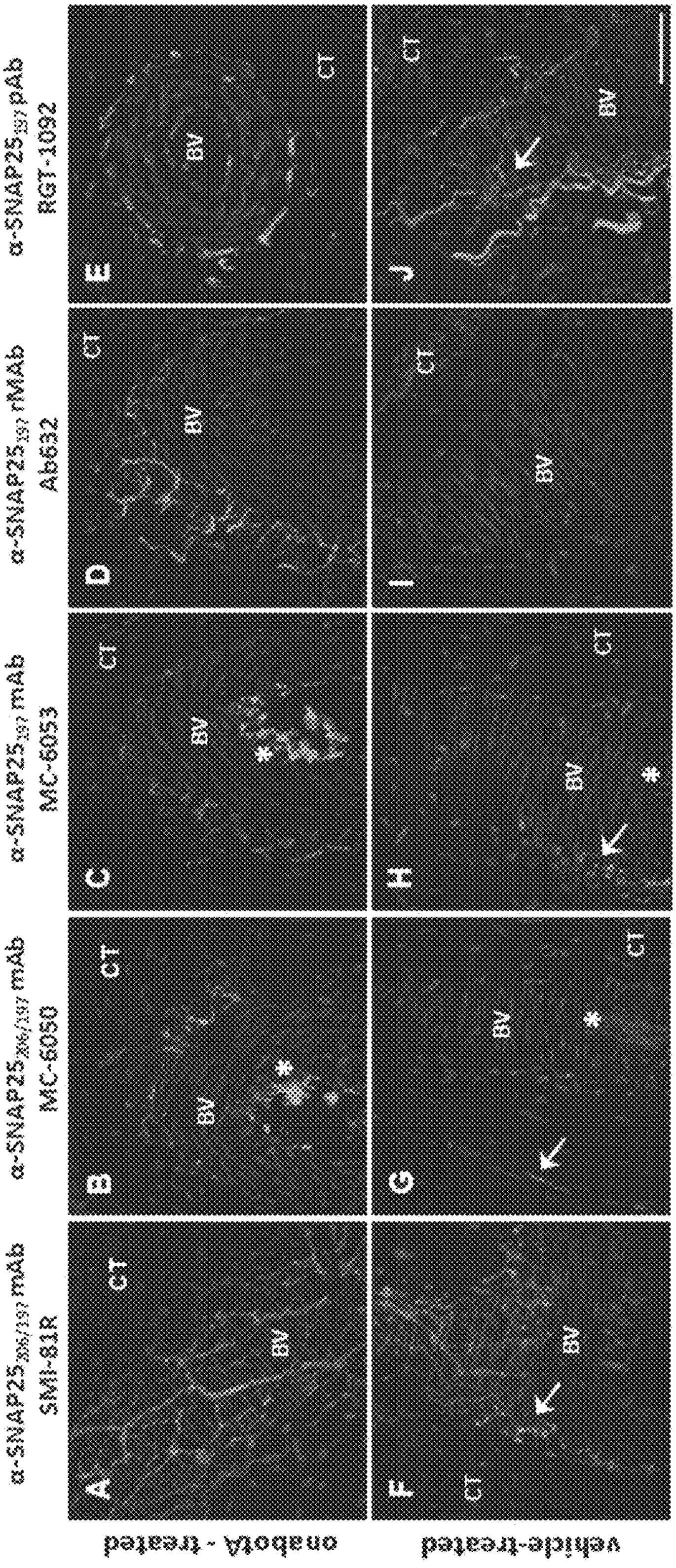
FIG. 6 (A-J) shows immunohistochemical analysis comparing the specificity of antibodies against SNAP25 in sections of rat glabrous skin following treatment with either onabotulinumtoxinA (30 U/kg) or vehicle. (A-E) Confocal images of rat skin injected with onabotulinumtoxinA and probed with (A) commercial mAb (SMI-81R) against full-length (206) and cleaved (197) SNAP25, (B) a second commercial mAb (MC-6050) against $SNAP25_{197}$ & $SNAP25_{206}$, (C) commercial mAb (MC-6053) against $SNAP25_{197}$, (D) Ab632-rMAb against $SNAP25_{197}$ and (E) RGT-1092 pAb against $SNAP25_{197}$. (F-J) Confocal images of control rat skin injected with vehicle and probed with the same five antibodies. Arrows (F, G, H and J) point to IR-signal within nerve fibers from vehicle treated rat skin. Asterisks (B, C, G and H) point to non-specific IR-signal within the lumen of blood vessels. BV, blood vessel; CT, connective tissue; Scale bar=50 μm.

FIG. 6 shows immunohistochemical analysis comparing the specificity of antibodies against SNAP25 in sections of rat glabrous skin following treatment with either onabotulinumtoxinA (30 U/kg) or vehicle. (A-E) Confocal images of rat skin injected with onabotulinumtoxinA and probed with (A) commercial mAb (SMI-81R) against full-length (206) and cleaved (197) SNAP25, (B) a second commercial mAb (MC-6050) against SNAP25197 & $SNAP25_{206}$, (C) commercial mAb (MC-6053) against $SNAP25_{197}$, (D) Ab632-rMAb against $SNAP25_{197}$ and (E) RGT-1092 pAb against $SNAP25_{197}$. (F-J) Confocal images of control rat skin injected with vehicle and probed with the same five antibodies. Arrows (F, G, H and J) point to IR-signal within nerve fibers from vehicle treated rat skin. Asterisks (B, C, G and H) point to non-specific IR-signal within the lumen of blood vessels. BV, blood vessel; CT, connective tissue; Scale bar=50 μm.

FIG. 7. shows immunohistochemical analysis comparing the specificity of antibodies against SNAP25 in skeletal muscle underlying rat glabrous skin following treatment with either onabotulinumtoxinA (30 U/kg) or vehicle. (A-D) Confocal images showing motor nerve terminals (MNT, arrows) within the underlying muscle of the rat paw injected with onabotulinumtoxinA and probed with (A) commercial mAb (SMI-81R) against full-length (206) and cleaved (197) SNAP25; (B) a second commercial mAb (MC-6050) against $SNAP25_{197}$ & $SNAP25_{206}$; (C) a commercial mAb (MC-6053) against $SNAP25_{197}$ and (D) Ab632-rMAb against $SNAP25_{197}$; (E-H) Confocal images from control rat paw injected with vehicle and probed with the same four antibodies. SNAP25-IR signal is in green (shown as gray in black and white drawings) and DIC illumination was used to delineate the underlying muscle fibers (MF). Arrow (E) points to IR-signal within a MNT from vehicle treated rat paw; asterisks (B, C, F and G) point to non-specific IR-signal within the muscle. Scale bar=50 μm.

Figure 8:
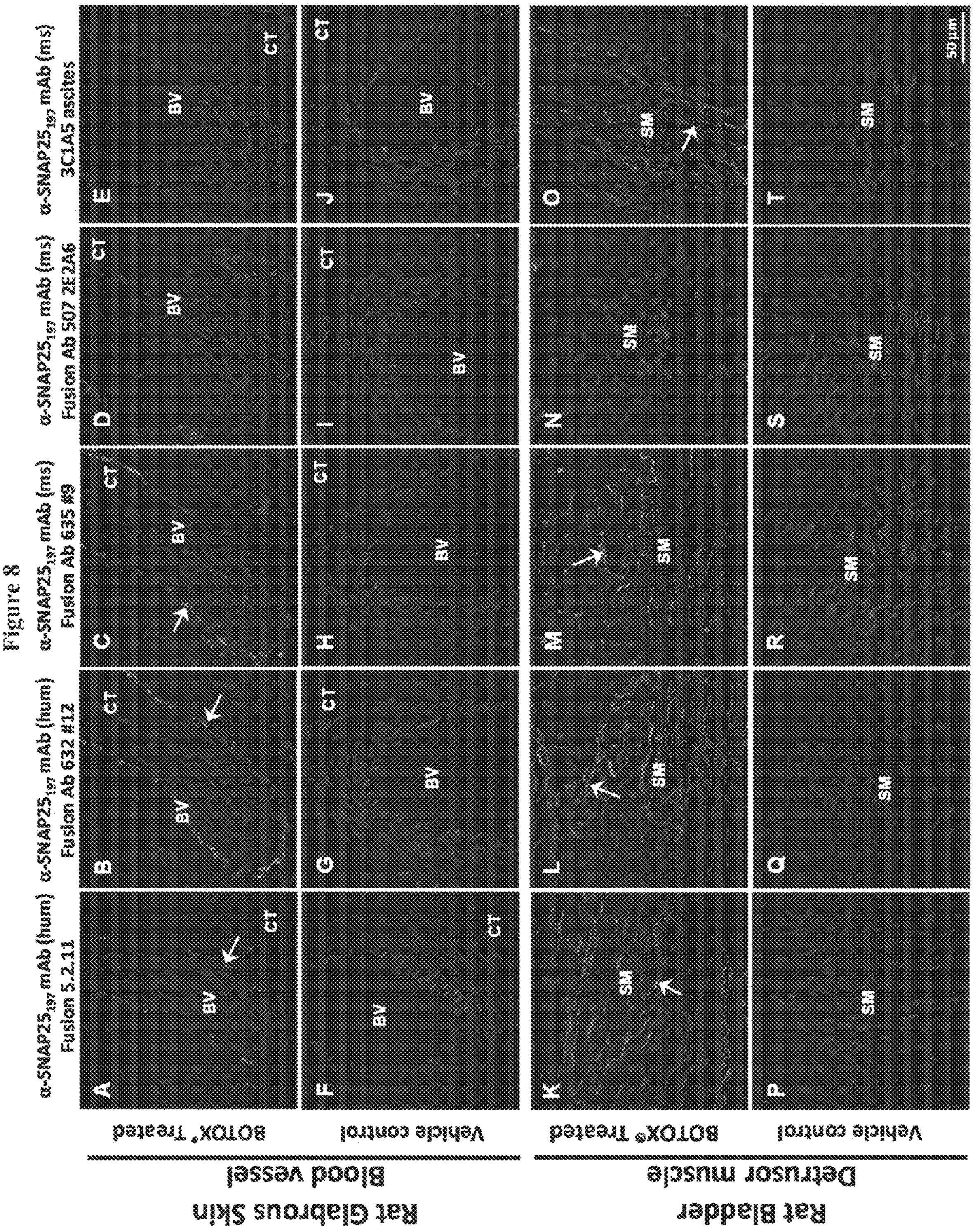
FIG. 8 (A-T) shows immunohistochemical analysis comparing the specificity of various $SNAP25_{197}$-specific antibodies in sections of rat glabrous skin (FIGS. 7A-7J) and rat bladder (FIGS. 7K-7T) following treatment with either BOTOX® or vehicle. (A-J) Confocal images of rat skin injected with BOTOX® and probed with (A) an older generated lot (May 2, 2011) of the humanized Ab632-rMAb, (B) a more recent lot of humanized Ab632-rMAb, (C) a recent lot of the murine Ab635-rMAb, (D) the Ab507 mAb (clone 2E2A6 used for the Cell-Based Assay in 18383-CIP), and (E) the original 'non-recombinant' 3C1A5 mAb purified from ascites. (F-J) Confocal images of control rat skin injected with vehicle and probed with the same five antibodies. Arrows (A, B, C) point to specific immunoreactive-signal within nerve fibers surrounding blood vessels. (K-T) Confocal images of bladder smooth muscle (SM) injected with BOTOX® and probed with (K) an older generated lot (May 2, 2011) of the humanized Ab632-rMAb, (L) a more recent lot of humanized Ab632-rMAb, (M) a recent lot of the murine Ab635-rMAb, (N) the Ab507 mAb (clone 2E2A6 used for the Cell-Based Assay in 18383-CIP), and (0) the original 'non-recombinant' 3C1A5 mAb purified from ascites. (P-T) Confocal images of control rat bladder injected with vehicle and probed with the same five antibodies. Arrows (K, L, M and O) point to specific immunoreactive-signal in nerve fibers within the bladder smooth muscle. BV, blood vessel; CT, connective tissue; SM, detrusor muscle. Scale bar=50 μm.

FIG. 8 shows immunohistochemical analysis comparing the specificity of $SNAP25_{197}$-specific antibodies in sections of rat glabrous skin (A-J) and rat bladder (K-T) following treatment with BOTOX® or vehicle. (A-E) Confocal images of rat skin following BOTOX® injection show IR-signal for $SNAP25_{197}$ in nerve fibers surrounding blood vessels with all the rMAbs (old and new batches, arrow). The 2E2A6 clone (Ab507) and the 3C1A5 ascites antibodies both failed to detect any $SNAP25_{197}$ signal in this tissue. (F-J) In vehicle-treated controls, no SNAP25-IR is detected with any of the antibodies. (K-O) $SNAP25_{197}$-IR signal is detected in the nerve fibers coursing through the detrusor muscle in rat bladder (arrows) following BOTOX® treatment with all the antibodies except the 2E2A6 clone. (P-T) In vehicle-treated controls, no $SNAP25_{197}$-IR is detected with any of the antibodies. BV, blood vessel; CT, connective tissue; SM, smooth muscle.

Example 3. Immunohistochemical Comparison—Human Tissue

Among the commercially available antibodies against SNAP25, the MC-6053 monoclonal antibody targeting $SNAP25_{197}$ is most similar to our murine Ab635-rMAb with regard to the type and species of antibody (Table 1). We therefore performed a head-to-head comparison of the SNAP25-IR expression patterns between our Ab635-rMAb and the MC-6053 mAb in biopsy samples of onabotulinumtoxinA and saline-treated human back skin. The presumption was that since this was a probe of human tissue using a mouse antibody, the non-specific IR-signal (regardless of the source) would be minimal.

Human skin biopsy samples were obtained through a Phase 1 Allergan clinical study. The study was conducted in accordance with the guidelines and regulations for Good Clinical Practice and all relevant local and country privacy guidelines. The study protocol, informed consent, and all appropriate study-related documents were approved by the Institutional Review Board/Ethics Committee.

Adult human back skin was injected ID with either 10 U of onabotulinumtoxinA or vehicle. Punch biopsy samples from back skin were harvested 14-days post-treatment and fixed overnight in the same fixative. Tissues were washed and cryoprotected in 30% sucrose/PBS solution overnight at 4° C. Skin samples were hemisected along the midline, embedded in O.C.T. (Tissue-Tek) and stored frozen at −80° C. until sectioning. Tissue blocks were cryostat-sectioned (14 μm-thick), slide-mounted and slides were kept at −20° C. until use. IHC and data analysis was performed as outlined above.

Figure 9:
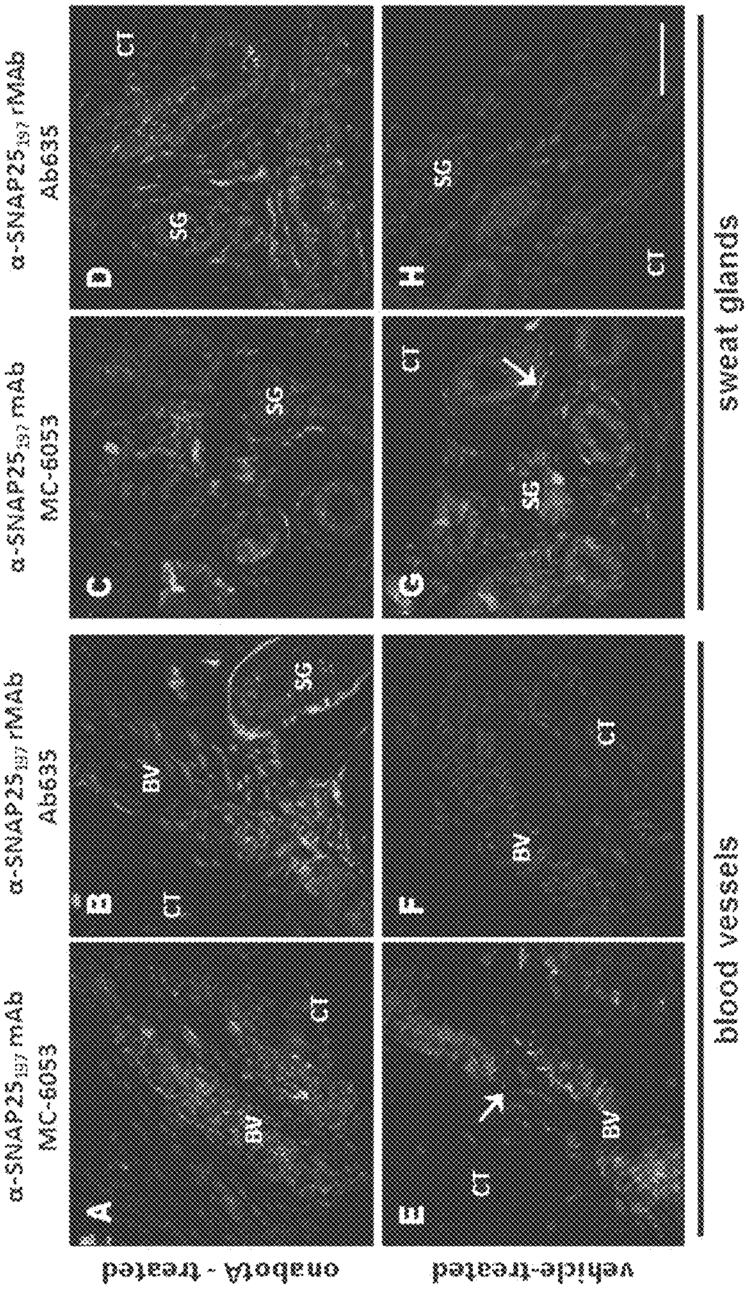
FIG. 9 (A-H) shows immunohistochemical comparison of the commercially-available (MC-6053) mAb against $SNAP25_{197}$ vs. Ab635-rMAb in sections of human back skin following treatment with either onabotulinumtoxinA (10U) or vehicle. Confocal images of blood vessels in onabotulinumtoxinA (A, B) and vehicle-treated (E, F) human skin probed with either (A, E) the MC-6053 mAb or (B, F) Ab635-rMAb. Sweat glands in onabotulinumtoxinA (C, D) and vehicle-treated (G, H) human skin probed with either (C, G) the MC-6053 mAb or (D, H) Ab635-rMAb. Arrows point to IR-signal within nerve fibers from vehicle treated human skin. BV, blood vessel; CT, connective tissue; SG, sweat gland; Scale bar=50 μm.

In the human back skin, the IR-signal for both antibodies was observed in nerve fibers surrounding blood vessels and sweat glands within the skin (FIG. 9). IR-signal for the MC-6053 mAb was observed in nerve fibers from both onabotulinumtoxinA and saline-treated back skin. In sharp contrast, IR-signal for our murine Ab635-rMAb was only observed in nerve fibers from onabotulinumtoxinA-treated, but not saline-treated human back skin (FIG. 9) demonstrating its superior specificity and more importantly, its utility as a clinical diagnostics tool.

FIG. 9 shows immunohistochemical comparison of the commercially-available (MC-6053) mAb against $SNAP25_{197}$ vs. Ab635-rMAb in sections of human back skin following treatment with either onabotulinumtoxinA (10 U) or vehicle. Confocal images of blood vessels in onabotulinumtoxinA (A, B) and vehicle-treated (E, F) human skin probed with either (A, E) the MC-6053 mAb or (B, F) Ab635-rMAb. Sweat glands in onabotulinumtoxinA (C, D) and vehicle-treated (G, H) human skin probed with either (C, G) the MC-6053 mAb or (D, H) Ab635-rMAb. Arrows point to IR-signal within nerve fibers from vehicle treated human skin. BV, blood vessel; CT, connective tissue; SG, sweat gland; Scale bar=50 μm.

Given the difficulty in detecting BoNT/A location and movement within cells, the proprietary recombinant humanized a-$SNAP25_{197}$ and proprietary recombinant murine a-$SNAP25_{197}$ can be used to cross detect $SNAP25_{197}$ in the other species. While other a-SNAP25 antibodies are capable of detection, using recombinant murine a-$SNAP25_{197}$ to detect $SNAP25_{197}$ in human tissue or using recombinant humanized a-$SNAP25_{197}$ to detect $SNAP25_{197}$ in murine allows for in-depth analysis of BoNT/A mechanism of action not possible with other available antibodies.

Example 4. Immunocytochemical Comparison

Some antibodies may work better for one assay/indication over another. Therefore, in order to complete our analysis, we compared the IR-signal from several of the antibodies in DRG cell cultures that were treated with either BoNT/A (3 nM) or saline.

DRG cell cultures were prepared and treated as outlined above. Immunocytochemistry and data analysis was performed as detailed above.

As in the tissues, the SMI-81R antibody showed strong IR-signal in both BoNT/A and saline-treated cultures (FIG. 10A, D). Both the MC-6053 commercially available mAb and our human Ab632-rMAb demonstrated specific $SNAP25_{197}$-IR signal in neuronal cells from BoNT/A-treated cultures (FIG. 10B, C). No signal was detected in saline-treated cultures (FIG. 10E, F). However, the MC-6053 mAb exhibited a faint background signal over the neuronal soma in the saline-treated cultures (FIG. 10E).

Figure 10:
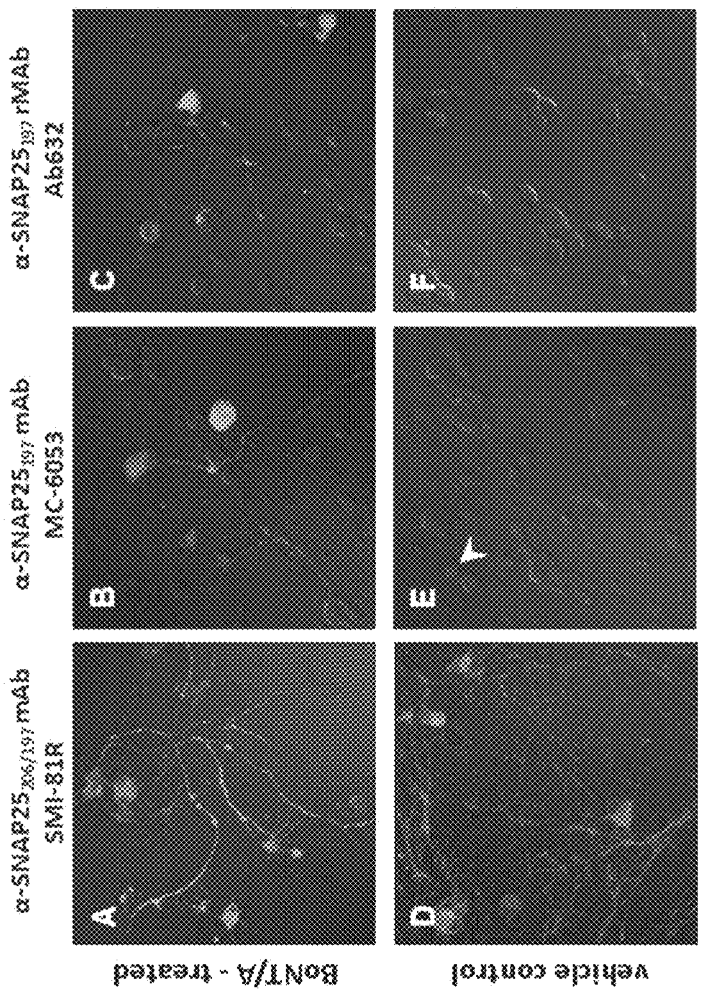
FIG. 10 (A-F) shows confocal images of BoNT/A (3 nM)- or vehicle-treated dorsal root ganglia (DRG) cultures probed with antibodies to different forms of SNAP25. (A-C) DRG cultures exposed to BoNT/A for 3 hr and later stained with (A) commercial (SMI-81R) mAb against full-length (206) and cleaved (197) SNAP25, (B) commercial (MC-6053) mAb against $SNAP25_{197}$ and (C) Ab632-rMAb against $SNAP25_{197}$. (D-F) Control DRG cultures exposed to vehicle and probed with the same three antibodies. Arrowhead in E points to a neuronal soma exhibiting background labeling.

FIG. 10 shows confocal images of BoNT/A (3 nM)- or vehicle-treated dorsal root ganglia (DRG) cultures probed with antibodies to different forms of SNAP25. (A-C) DRG cultures exposed to BoNT/A for 3 hr and later stained with (A) commercial (SMI-81R) mAb against full-length (206) and cleaved (197) SNAP25, (B) commercial (MC-6053) mAb against $SNAP25_{197}$ and (C) Ab632-rMAb against $SNAP25_{197}$. (D-F) Control DRG cultures exposed to vehicle and probed with the same three antibodies. Arrowhead in E points to a neuronal soma exhibiting background labeling.

The presence of active BoNT/A in cells expressing SNAP25 can often be determined by using a selective antibody against the cleaved substrate ($SNAP25_{197}$). In the present study, we introduce several rMAbs that were developed in-house against $SNAP25_{197}$ and compared their immuno-reactive signal against that of commercial antibodies using a variety of different methods (Table 3). Both our human and murine rMAbs consistently detected $SNAP25_{197}$ in all assays and on different tissues, and as expected, did not detect full-length SNAP25 ($SNAP25_{206}$). This was not the case with other purportedly $SNAP25_{197}$-selective antibodies, which displayed variable assay-dependent specificity. These results confirm that the BoNT/A-cleaved SNAP25 epitope is difficult to target specifically with an antibody without also recognizing the intact SNAP25 protein, which could lead to potential misinterpretation of results if the proper controls are not in place. Therefore, any given $SNAP25_{197}$ antibody should be tested under multiple conditions and tissue types to ensure its fidelity in detecting the presence of BoNT/A-cleaved SNAP25.

Site-specific antibodies are increasingly being used for both in vitro and in vivo analysis. These antibodies can detect sites of phosphorylation or sites of enzymatic cleavage and are invaluable tools for our understanding of the maturation, activity and degradation of proteins (Mort, J. S. and Buttle, D. J., 1999. The use of cleavage site specific antibodies to delineate protein processing and breakdown pathways. Mol. Pathol. 52, 11-18.; Mort, J. S., Flannery, C. R., Makkerh, J., Krupa, J. C., and Lee, E. R., 2003. Use of anti-neoepitope antibodies for the analysis of degradative events in cartilage and the molecular basis for neoepitope specificity. Biochem. Soc. Symp. 107-114.; Nagata, K., Izawa, I., and Inagaki, M., 2001. A decade of site- and phosphorylation state-specific antibodies: recent advances in studies of spatiotemporal protein phosphorylation. Genes Cells 6, 653-664.). Within the field of botulinum neurotoxins, cleavage site-specific antibodies can help detect the activity of minute quantities of BoNT light-chain that may otherwise be very difficult to perceive. To that end, the use of polyclonal antibodies may be of limited value because a mixed immunoglobulin population could be produced, not all of which would have the required specificity for the cleavage epitope (Mort, J. S. and Buttle, D. J., 1999. The use of cleavage site specific antibodies to delineate protein processing and breakdown pathways. Mol. Pathol. 52, 11-18.). Furthermore, the peptide antigen should be relatively short in order to reduce the possibility of generating antibodies that bind to a part of the sequence remote from the target epitope.

The anti-$SNAP25_{197}$ mAb presented in the current study was initially screened and selected for its superior performance in IHC assays. The rMAbs (Ab632 and Ab635) that were subsequently generated from this antibody demonstrated superb specificity to BoNT/A-cleaved SNAP25 in several different assays, including IHC. Furthermore, these rMAbs showed superior $SNAP25_{197}$ specificity compared to other antibodies tested (Table 3). Accordingly, our rMAbs represent effective new tools for the detection of BoNT/A activity within cells and in clinical samples, and will be utilized in future studies to characterize the efficacy of BoNT/A in tissues of interest. The specific sequences for these antibodies are presented in Table 2 above.

Overall, the antibodies tested in Western blot assays, immunohistochemistry on tissues and immunocytochemistry on cells showed various specificity to BoNT/A cleaved SNAP25 ($SNAP25_{197}$) and uncleaved SNAP25 ($SNAP25_{206}$). A summary of the results are shown in Table 3 below.

TABLE 3

Summarized Results of Antibody Specificity to full length SNAP25 (206) or BoNT/A-cleaved SNAP25 (197).

| Antibody | Specificity | Western Blot | Rat bladder | Rat skin | Human skin | Rat DRG culture |
|---|---|---|---|---|---|---|
| SMI-81R | $SNAP25_{206/197}$ | 206 + 197 | 206 + 197 | 206 + 197 | n/t | 206 + 197 |
| MC-6050 | $SNAP25_{206/197}$ | 197 | 197 | 206 + 197 + b | n/t | n/t |
| MC-6053 | $SNAP25_{197}$ | 197 | 197 | 206 + 197 + b | 206 + 197 | 197 + b |
| Ab632 | $SNAP25_{197}$ | 197 | 197 | 197 | n/t | 197 |
| Ab635 | $SNAP25_{197}$ | 197 | 197 | n/t | 197 | n/t |
| RGT-1092 | $SNAP25_{197}$ | 197 | 206 + 197 | 206 + 197 | n/t | n/t |

n/t = not tested;
b = background

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

We claim:

1. A recombinant anti-SNAP25 (synaptosomal-associated protein, 25 kDa) antibody, wherein the antibody binds preferentially to BoNT/A (botulinum neurotoxin serotype A) cleaved SNAP25; and wherein the antibody is a recombinant murine antibody and comprises the heavy chain sequence of SEQ ID NO: 3 and the light chain sequence of SEQ ID NO:1; or wherein the antibody is a recombinant human antibody and comprises the heavy chain sequence of SEQ ID NO:7 and the light chain sequence of SEQ ID NO:5.

2. The anti-SNAP25 antibody of claim 1, wherein the antibody binds BoNT/A cleaved SNAP25 in a tissue sample.

3. The anti-SNAP25 antibody of claim 2, wherein the tissue sample is a biopsy sample.

4. The anti-SNAP25 antibody of claim 1, wherein the antibody does not bind to full length SNAP25.

5. A method of determining if a tissue has been exposed to BoNT/A enzymatic activity comprising contacting a tissue sample suspected of having been exposed to BoNT/A (botulinum neurotoxin serotype A) enzymatic activity with an anti-SNAP25 antibody wherein the antibody binds preferentially to BoNT/A cleaved SNAP25; wherein the antibody is a recombinant murine antibody and comprises the heavy chain sequence of SEQ ID NO: 3 and the light chain sequence of SEQ ID NO: 1, or wherein the antibody is a recombinant human antibody and comprises the heavy chain sequence of SEQ ID NO:7 and the light chain sequence of SEQ ID NO:5;

and detecting the presence of anti-SNAP25 antibody bound to the tissue sample, wherein the presence of the anti-SNAP25 antibody bound to the tissue sample indicates that the tissue sample has been exposed to BoNT/A activity.

6. The method of claim 5, wherein the antibody binds BoNT/A cleaved SNAP25 in a tissue sample.

7. The method of claim 6, wherein the tissue sample is a biopsy sample.

8. The method of claim 5, wherein the antibody does not bind to full length SNAP25.

9. A kit for determining if a tissue sample has been exposed to BoNT/A enzymatic activity comprising a recombinant anti-SNAP25 antibody of claim 1.

10. The kit of claim 9, wherein the tissue sample is a biopsy sample.

11. The kit of claim 9, wherein the antibody does not bind to full length SNAP25.

* * * * *